US012685563B2

(12) United States Patent
Cundiff et al.

(10) Patent No.: US 12,685,563 B2
(45) Date of Patent: Jul. 21, 2026

(54) SURGICAL SYSTEMS AND METHODS INCLUDING ALIGNING GUIDES FOR PERFORMING A PERCUTANEOUS BUNION CORRECTION

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Eli W. Jacobson, Chandler, AZ (US)

(73) Assignee: Fusion Orthopedics USA, LLC, Mesa, AZ (US)

( * ) Notice: Subject to any disclaimer, the term of this patent is extended or adjusted under 35 U.S.C. 154(b) by 32 days.

(21) Appl. No.: 18/774,589

(22) Filed: Jul. 16, 2024

(65) Prior Publication Data

US 2026/0020880 A1      Jan. 22, 2026

(51) Int. Cl.
 *A61B 17/56*  (2006.01)
 *A61B 17/16*  (2006.01)
 (Continued)

(52) U.S. Cl.
 CPC .......... *A61B 17/56* (2013.01); *A61B 17/7291* (2013.01); *A61B 17/1682* (2013.01); *A61B 17/1703* (2013.01); *A61B 17/1714* (2013.01); *A61B 17/1717* (2013.01); *A61B 17/1732* (2013.01); *A61B 17/1735* (2013.01);
 (Continued)

(58) Field of Classification Search
 CPC ..... A61B 17/56; A61B 17/7291; A61B 17/72; A61B 17/1682; A61B 17/1662; A61B 17/17; A61B 17/1717; A61B 17/1732; A61B 17/1735; A61B 17/1739; A61B 17/1775; A61B 17/1782; A61B 17/1785;
 A61B 17/16; A61B 17/1703; A61B 17/1746; A61B 17/175; A61B 17/1714; A61B 17/1764; A61B 17/1796; A61B 2017/564; A61B 2017/565
 USPC ... 606/60, 62, 79–80, 86 R, 87, 96–98, 103, 606/916
 See application file for complete search history.

(56) References Cited

U.S. PATENT DOCUMENTS 4,781,182 A * 11/1988 Purnell .............. A61B 17/1714
               606/96
11,000,298 B1  5/2021 Graziano
     (Continued)

FOREIGN PATENT DOCUMENTS

CN  213430480 U  6/2021
CN  217566269 U  10/2022
CN  218899661 U  4/2023

OTHER PUBLICATIONS

Novastep, Pecaplasty.

*Primary Examiner* — Marcela I. Shirsat

(57) ABSTRACT

Surgical systems and methods for correcting a bunion percutaneously including aligning guides are provided herein. At least one embodiment includes a handle including a rod with a first end including a first longitudinal axis and a second end including a second longitudinal axis offset from the first longitudinal axis. The handle can couple to a gadget including a leg that couples to the handle, and a translator that extends and retracts the leg. The gadget can also a slide with a guide body to guide a guide wire for accurate placement of a screw. The surgical system can also include a periscope to assist in pre-visualization of the screw placement.

17 Claims, 23 Drawing Sheets

(51) Int. Cl.
  A61B 17/17     (2006.01)
  A61B 17/72     (2006.01)
(52) U.S. Cl.
  CPC ....... *A61B 17/1739* (2013.01); *A61B 17/1775*
      (2016.11); *A61B 17/1796* (2013.01); *A61B*
      *2017/564* (2013.01); *A61B 2017/565*
      (2013.01); *A61B 17/72* (2013.01)

(56)                References Cited

U.S. PATENT DOCUMENTS

| | | | |
|---|---|---|---|
| 11,045,239 | B2 | 6/2021 | Blitz |
| 11,207,113 | B2 | 12/2021 | Girod |
| 11,672,549 | B2 | 6/2023 | Cundiff |
| 11,931,088 | B2 | 3/2024 | Pyle |
| 11,980,396 | B2 | 5/2024 | Schaumann et al. |
| 2002/0165550 | A1* | 11/2002 | Frey ................... A61B 17/1671 |
| | | | 606/85 |
| 2008/0103506 | A1* | 5/2008 | Volpi ................ A61B 17/1764 |
| | | | 606/96 |
| 2013/0053959 | A1* | 2/2013 | Lizardi .............. A61B 17/1764 |
| | | | 623/13.14 |
| 2016/0074079 | A1* | 3/2016 | Leemrijse ........... A61B 17/809 |
| | | | 606/291 |
| 2020/0060698 | A1 | 2/2020 | Woodard |
| 2020/0093501 | A1* | 3/2020 | Patel .................. A61B 17/1717 |
| 2020/0281637 | A1* | 9/2020 | Denham .............. A61F 2/0805 |
| 2021/0315621 | A1 | 10/2021 | Blitz |
| 2022/0192685 | A1* | 6/2022 | Gazonnet ........... A61B 17/1775 |
| 2024/0164819 | A1 | 5/2024 | Blitz |

* cited by examiner

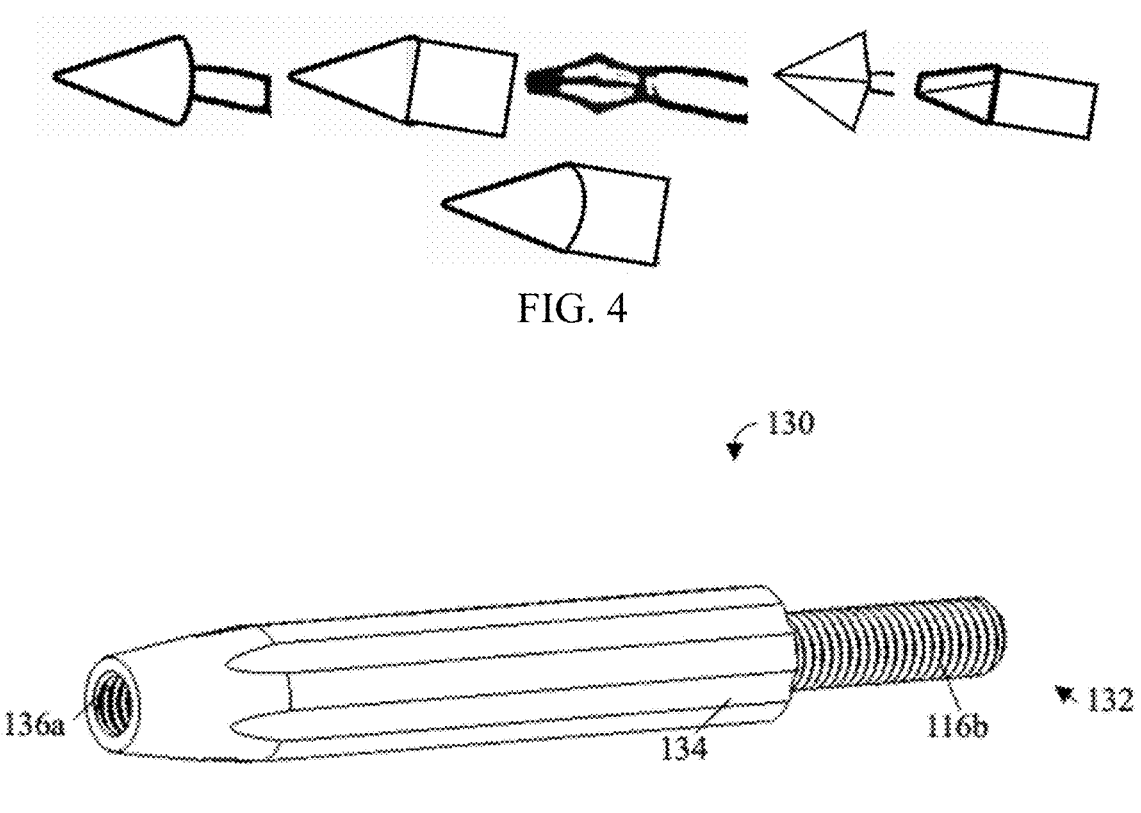
FIG. 4
FIG. 5
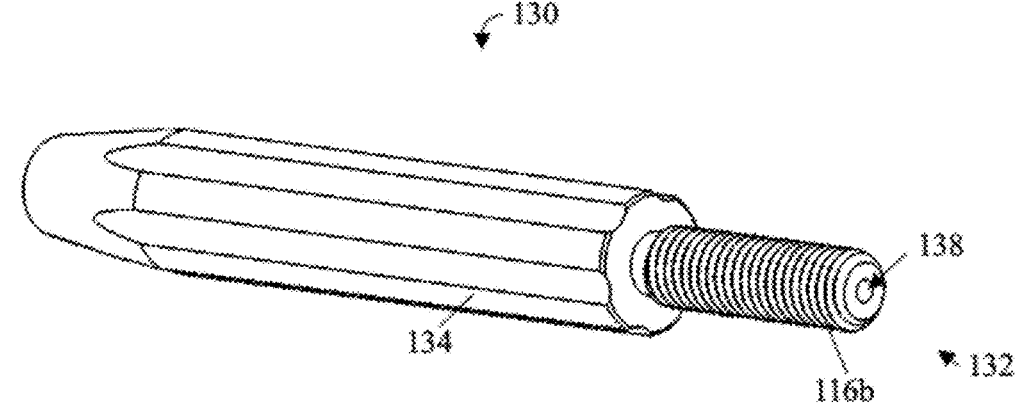
FIG. 6

FIG. 52

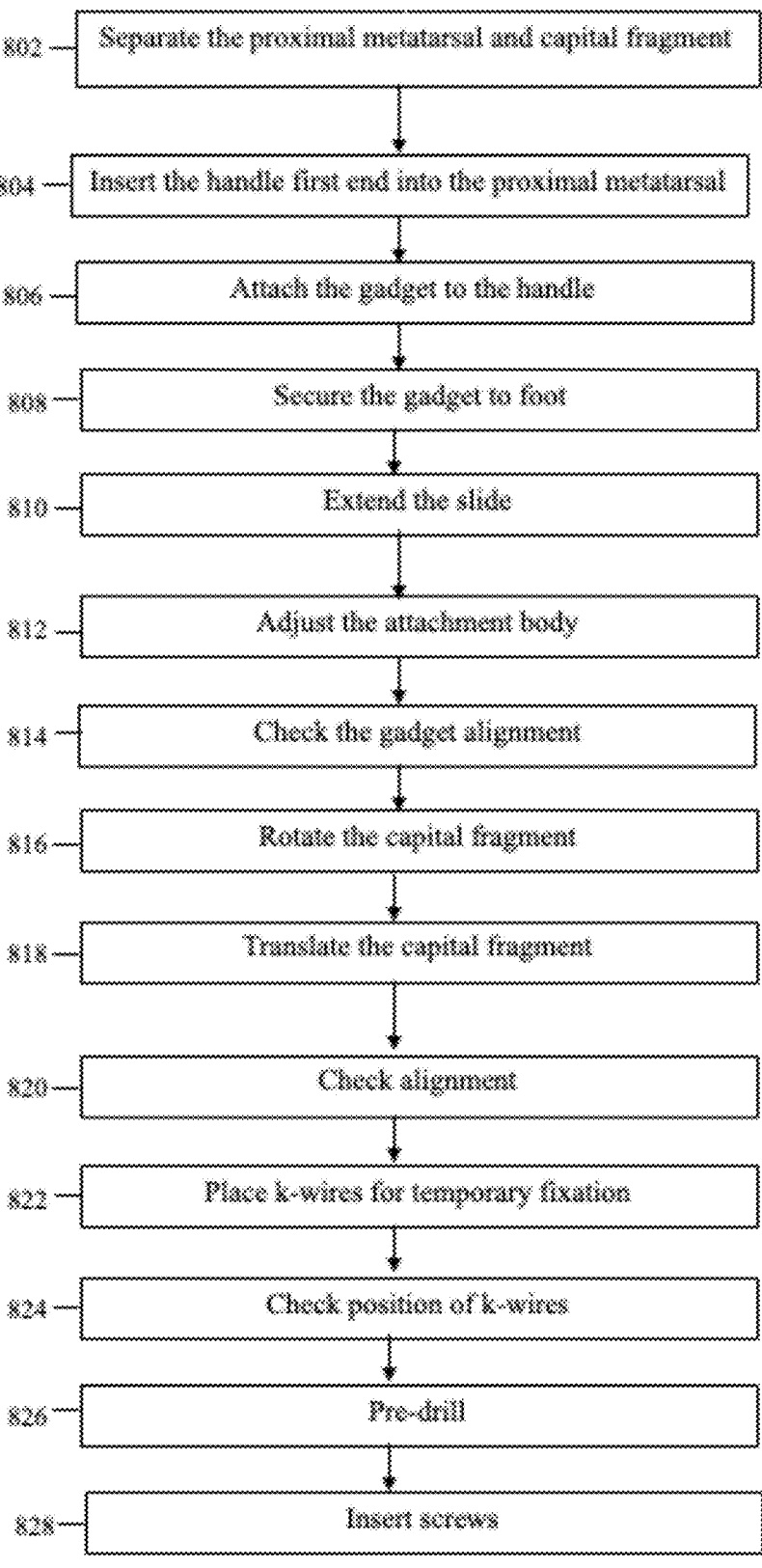

802 — Separate the proximal metatarsal and capital fragment

804 — Insert the handle first end into the proximal metatarsal

806 — Attach the gadget to the handle

808 — Secure the gadget to foot

810 — Extend the slide

812 — Adjust the attachment body

814 — Check the gadget alignment

816 — Rotate the capital fragment

818 — Translate the capital fragment

820 — Check alignment

822 — Place k-wires for temporary fixation

824 — Check position of k-wires

826 — Pre-drill

828 — Insert screws

SURGICAL SYSTEMS AND METHODS INCLUDING ALIGNING GUIDES FOR PERFORMING A PERCUTANEOUS BUNION CORRECTION

FIELD OF THE TECHNOLOGY

The present technology relates generally to surgical aligning guides, and more particularly to, surgical instruments and systems for a minimally invasive approach to bunion correction.

BACKGROUND

It is desirable to have a minimally invasive approach to a bunion correction surgery because it minimizes trauma to patient tissues which in turn positively effects patient outcomes. Minimally invasive surgical approaches are difficult because visual access to the surgical site is limited or restricted. In many procedures radiographs are used to visualize steps of the surgical procedure and portions of the patient's anatomy. In a chevron bunion correction, the placement of the bone screws requires a precision that is difficult to achieve with a radiograph. Thus, alignment tools would be helpful.

SUMMARY

A surgical apparatus that can include a handle, wherein the handle is configured to be couplable to a gadget. The handle can include: a rod including a first end and a second end that is opposite the first end, a first longitudinal axis of the first end, and a second longitudinal axis of the second end, wherein the first longitudinal axis is offset from the second longitudinal axis by an extension. The handle can also include a coupler removably coupled to the rod. The coupler can include a first end and a second end opposite the first end. The handle can include a head that can be coupled to the rod second end. The coupler second end can be coupled to the head. The first and second longitudinal axis can be parallel and an extension length apart, i.e. they are offset by a length of the extension. The extension length can be in the range of 2 mm-50 mm.

The surgical apparatus can also include a gadget. The gadget can include: a body that can include a leg that can be coupled to the handle through the coupler; a slide that can be slidably coupled to the body; a guide body that can be slidably coupled to the body and configure to hold a guide wire, and is configured to be rotatable. The slide can include a lock to prevent the slide from moving from a desired position. The lock can have a handle.

The surgical apparatus can also include a translator. The translator can be coupled to the leg of the body and it can be configured to extend and retract the leg through the activation of an activation mechanism. The activation mechanism can be a dial. The dial can be coupled to a threaded rod which is in turn coupled to a set of threads included on/in the leg. The turning of the dial turns the rod and the rod threads, which extends and retracts the leg through the leg threads.

The surgical apparatus can also include a radiograph positioning tool that can assist a user in determining if the gadget is in a correct position.

The surgical apparatus can also include a guide wire sheath coupled to the body and configured to guide a k-wire to a desired position.

The surgical apparatus can include a rotation arm. The rotation arm can be removably couplable to the body. The rotation arm is configured to hold a k-wire at angles that are in approximately 5° increments. It is also configured to assist in the rotation of a metatarsal capital fragment.

The surgical apparatus can include at least one radiograph positioning tool. The radiograph positioning tool can be two non-radio opaque bars that are configured to align when viewed in the transverse plane.

The surgical apparatus can include a periscope. The periscope can be couplable to the guide body, or it can be integral with the guide body. The periscope can hold a sight wire (k-wire) in the same orientation that a guidewire sheath will guide a k-wire, which can in turn guide at least one screw into at least one target bone and/or into a proximal portion of a metatarsal and a metatarsal capital fragment. The periscope can include a radiograph positioning tool.

A method of performing a bone alignment correction can include the following. A handle can be coupled to a first bone portion by inserting a rod first end into the first bone portion, a rod second end can be opposite the rod first end and can be coupled to a head. The head can be coupled to a coupler which can have a first end and a second end opposite the first end. The coupler second end can be coupled to the head. The coupler first end can be coupled to a gadget leg, thereby coupling the gadget to the handle. The gadget can also include a body. The body can include at least one aperture. A k-wire can be inserted through the aperture into a bone of a subject to secure the gadget. The gadget can include a slide which can be extended. The gadget can include a periscope which can be coupled to the guide body. The periscope can include a sight wire which can be inserted into at least one periscope sight aperture. The position of the sight wire can be checked radiographically. If the position of the sight wire is not a desired position, the slide and guide body positions can be adjusted to achieve a desired sight wire position. Guide wire(s) can be inserted through the guide wire sheath and into the foot of a subject to hold a desired position of the bones or bone portions. Screws can be inserted in the foot of a subject over the guide wire(s).

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which:

FIG. 4 is a schematic diagram illustrating an isometric view of various embodiments of a rod first end of the surgical system of FIG. 1;

FIGS. 5 and 6 are schematic diagrams illustrating isometric views of an embodiment of a coupler included in various embodiments of the surgical system of FIG. 1;

FIG. 52 is flowchart illustrating an embodiment of a method of using the surgical system.

DETAILED DESCRIPTION OF THE DRAWINGS

Figures 1, 2, 3:
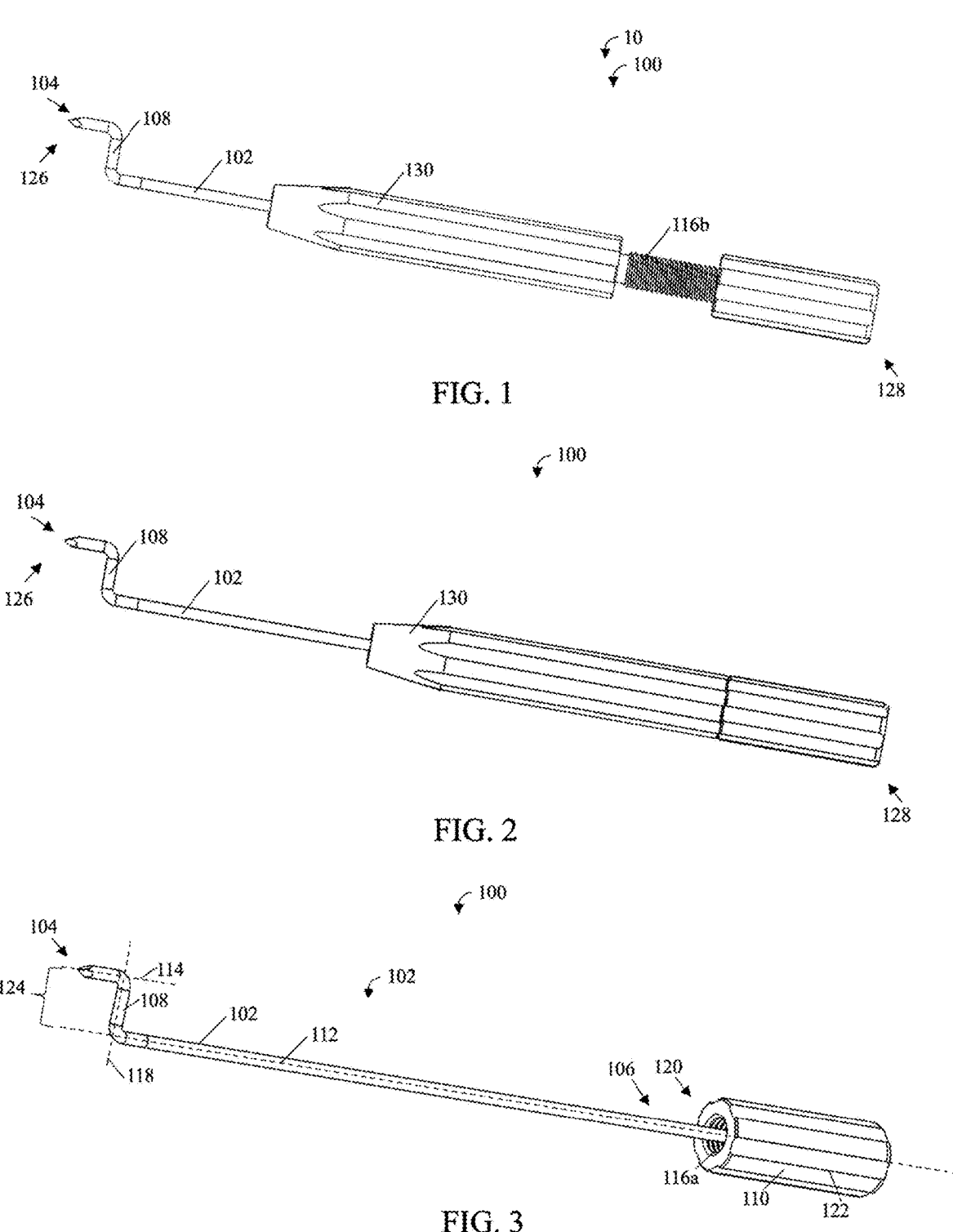
FIG. 1 is a schematic diagram illustrating an embodiment of a surgical system including a handle including a coupler in a first position.
FIG. 2 is a schematic diagram illustrating the surgical system of FIG. 1 with the coupler in a second position.
FIG. 3 is a schematic diagram illustrating an isometric view of the surgical system of FIG. 1 with the coupler removed.
Figure 7:
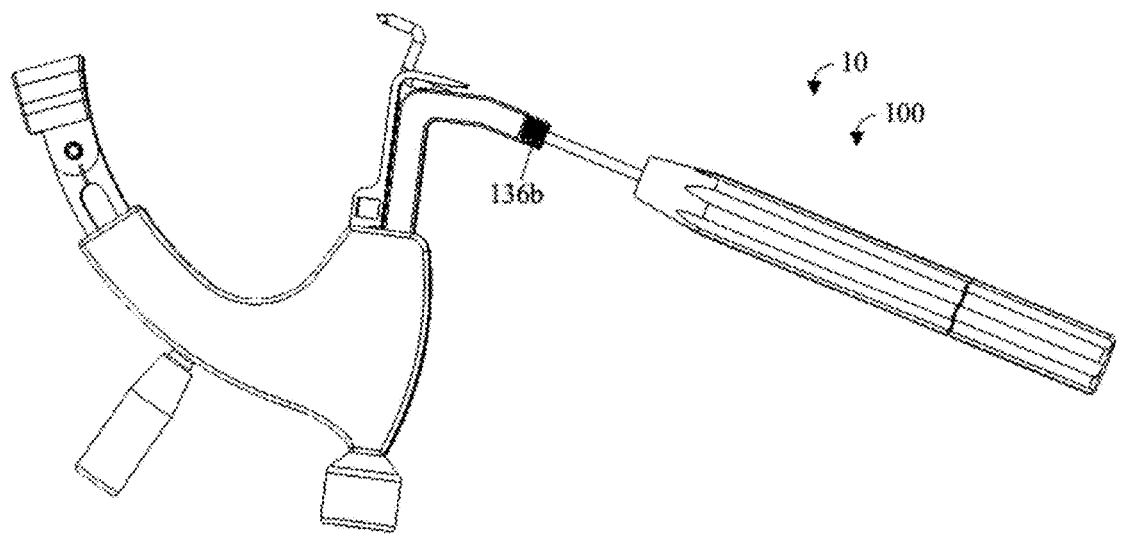
FIGS. 7 and 8 are schematic diagrams illustrating various embodiments of the surgical system including a gadget and a handle.
Figure 8:
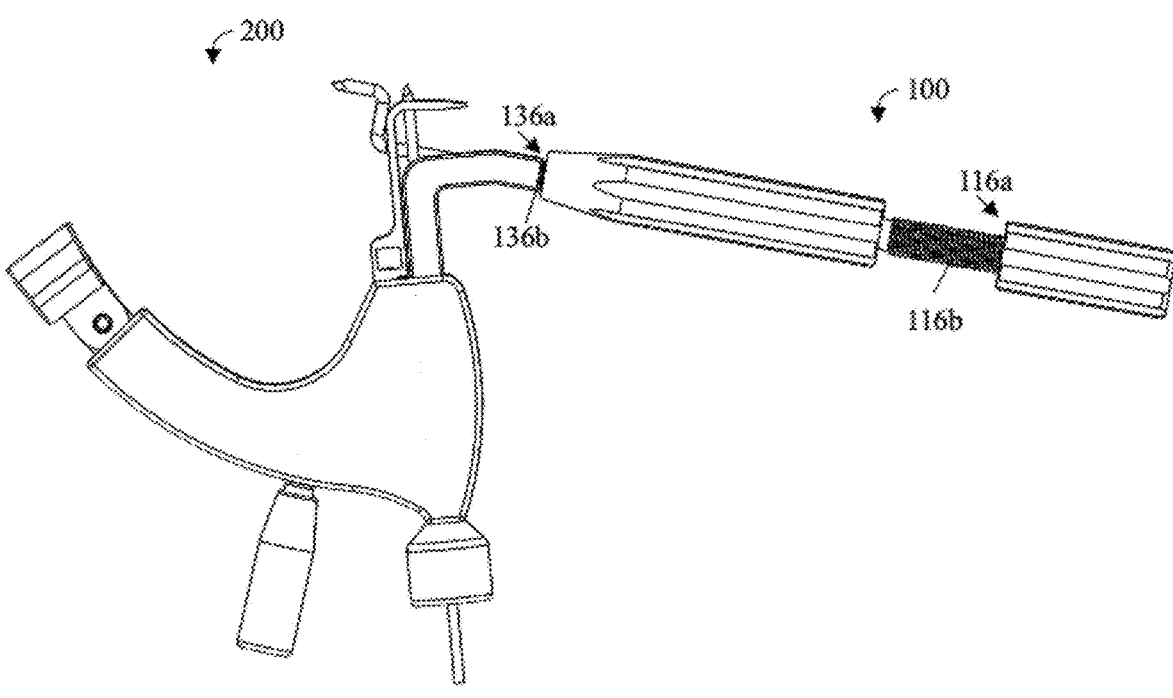
Figure 9:
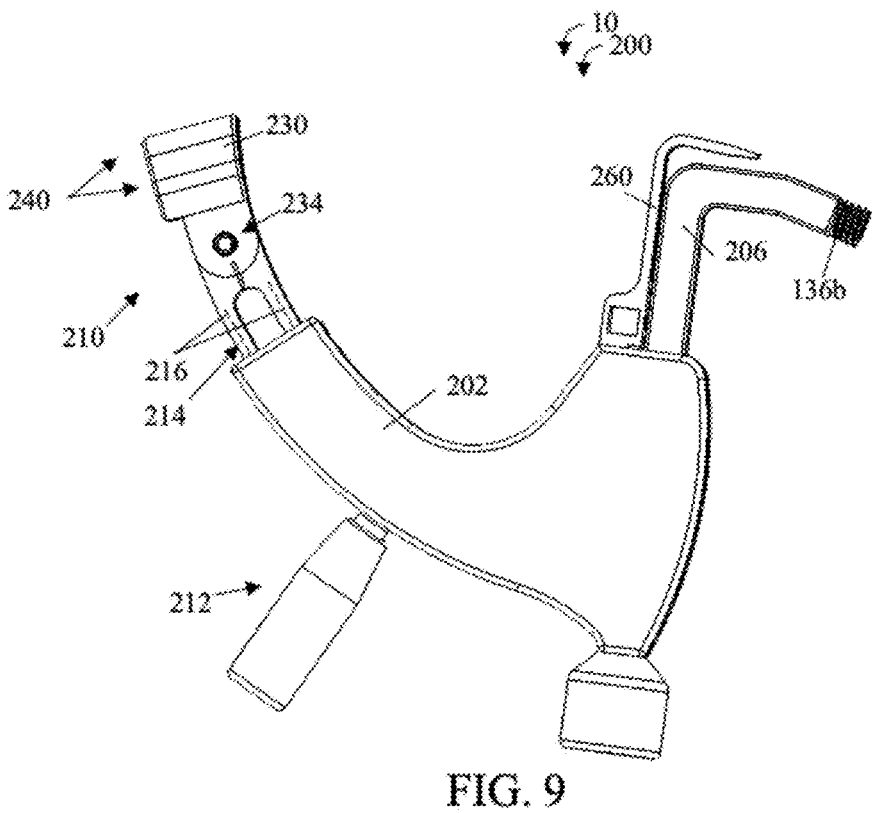
FIG. 9 is a schematic diagram illustrating a top view of an embodiment of a surgical system including a gadget.
Figure 10:
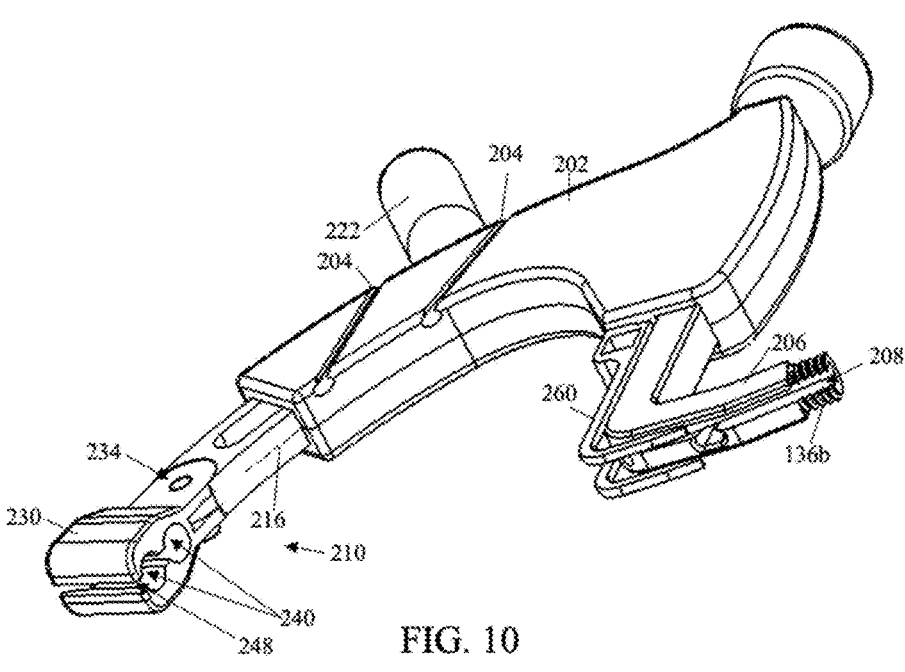
FIG. 10 is a schematic diagram illustrating an isometric view of an embodiment of the surgical system of FIG. 9 including a bottom of a gadget.
Figure 11:
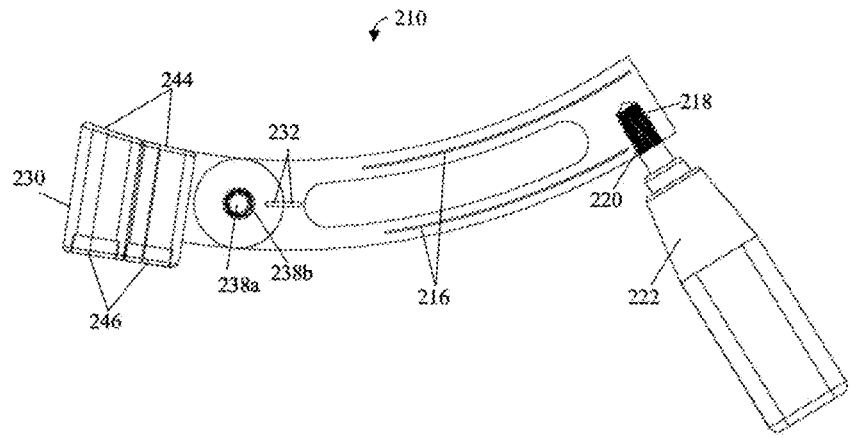
FIG. 11 is a schematic diagram illustrating a top view of an embodiment of the surgical system of FIG. 9 including a slide and a radiograph positioning tool.
Figure 12:
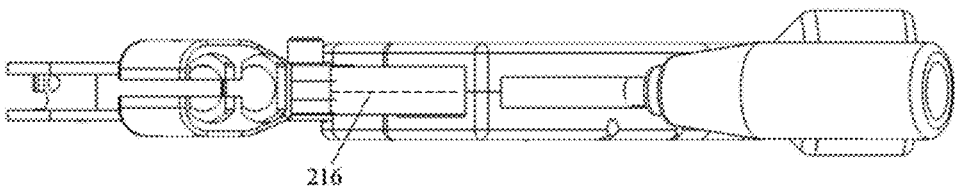
FIGS. 12 and 13 are schematic diagrams illustrating lateral views of various embodiments of the surgical system of FIG. 9 including a radiograph positioning tool.
Figure 13:
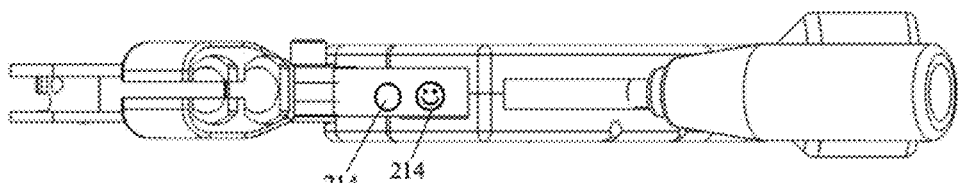
Figure 14:
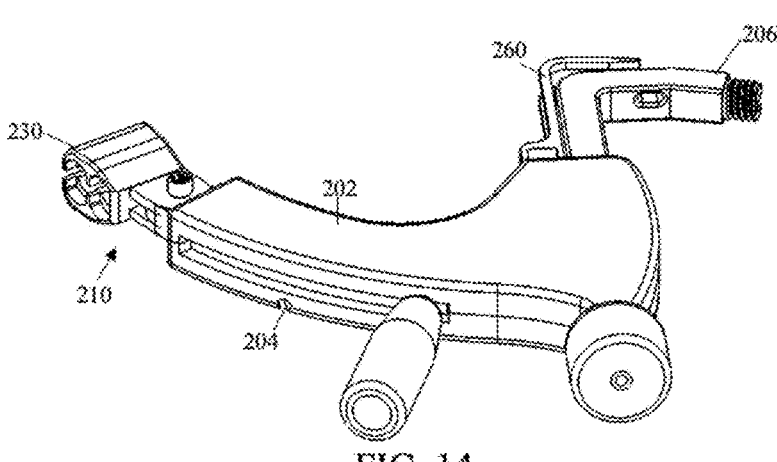
FIG. 14 is a schematic diagram illustrating an isometric view of the surgical system of FIG. 9 including a closed slide.
Figure 15:
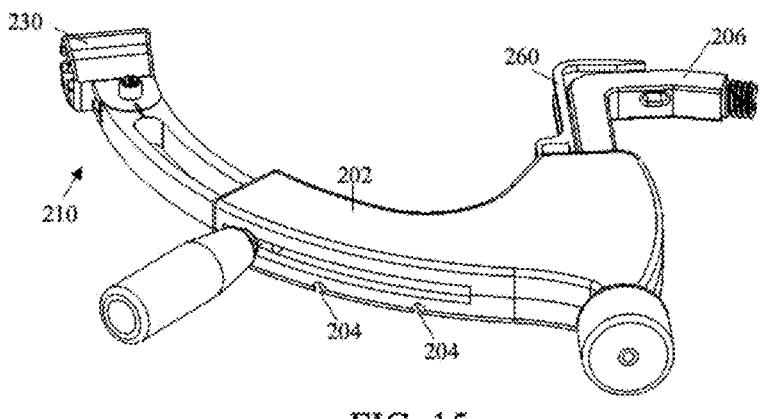
FIG. 15 is a schematic diagram illustrating an isometric view of the surgical system of FIG. 9 including a fully extended slide.
Figure 16:
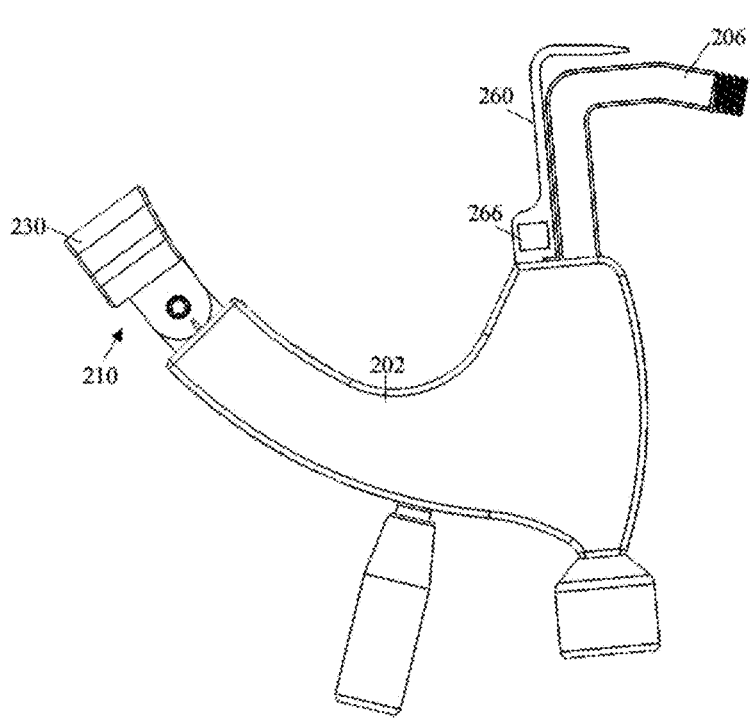
FIG. 16 is a schematic diagram illustrating a top view of the surgical system of FIG. 9 including a closed slide.
Figure 17:
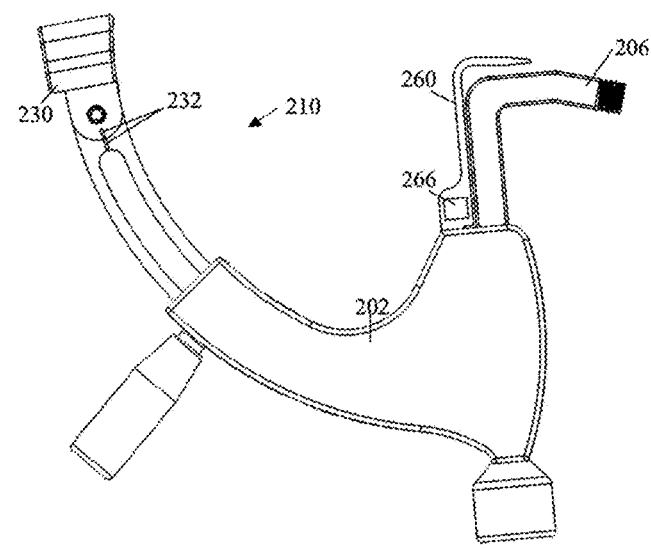
FIG. 17 is a schematic diagram illustrating a top view of the surgical system of FIG. 9 including a fully extended slide.

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "first bone" can refer to a bone or bone portion. The term "second bone" can refer to a bone that is a different bone than the first bone, or it can refer to a different portion of the same bone as the first bone.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. Aspects of the embodiments are described below with reference to schematic flowchart diagrams and/or schematic block diagrams of methods, apparatuses, and systems according to embodiments. The schematic flowchart diagrams and/or schematic block diagrams in the Figures illustrate the structure, functionality, and operation of possible implementations of apparatuses, systems, and methods according to various embodiments.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment.

The present technology may include any type of surgical system and is not limited to the style of surgical system depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1 through 51 are diagrams illustrating various views and/or embodiments of a surgical system 10. In various embodiments, the surgical system 10 can be utilized to perform a bone position correction procedure, such as a minimally invasive bunion correction procedure, or tailor's bunion correction procedure, among other bone alignment correction procedures, each of which is contemplated herein.

The surgical system 10 may be constructed of any suitable material that is capable of forming the various embodiments of the surgical system 10 described herein. In various embodiments, the surgical system 10 is constructed of a material that can be sterilized, and/or a material that is sterilized. In some embodiments, the surgical system 10 includes stainless steel, radio-opaque, titanium, titanium alloy, plastic(s), carbon fibers, and/or aluminum, among other suitable materials that are possible, each of which is contemplated herein. In additional or alternative embodiments, the surgical system 10 includes surgical grade stainless steel, among other suitable surgical grade materials that are possible, each of which is contemplated herein.

Referring now to FIGS. 1 through 8, at least in the illustrated embodiment, the surgical system 10 can include, among other components, a handle 100. The handle 100, in various embodiments, can include a rod 102, among other components.

The rod 102, in various embodiments, can include a first end 104 and a second end 106. The first end 104 can include, among other characteristics, a flat, blunt, wedged, conical, rounded, pointed, and/or spiked contour (e.g., see FIG. 4) among other contours, characteristics, and/or shapes that are possible, each of which is contemplated herein. In some embodiments the rod 102 can be straight such that the longitudinal axis 114 of the rod first end 104 is coextensive with the longitudinal axis 112 of the rod second end 106. The rod first end 104, in various embodiments, can be coupled to the rod second end 106, or they can be integral.

In some embodiments, the rod 102 can include an extension 108. The extension 108, in various embodiments, can be coupled to the rod first end 104 and/or to the rod second end 106, or they can be integral. The extension 108 can have a longitudinal axis 118 that is not coextensive with the longitudinal axis 112 of the rod second end 106. The extension 108, in at least some embodiments, can have a longitudinal axis 118 that is coextensive with the longitudinal axis 112 of the rod second end 106.

The rod extension longitudinal axis 118, in various embodiments, can be angled relative to the longitudinal axis 112 of the rod second end 106. The rod extension 108 longitudinal axis 118 can be perpendicular to the longitudinal axis 112 of the rod second end 106.

In additional or alternative embodiments, the rod extension 108 longitudinal axis 118 can be angled relative to the longitudinal axis 114 of the rod first end 104. The rod extension 108 longitudinal axis 118 can be perpendicular to the longitudinal axis 114 of the rod first end 104. In some embodiments, the longitudinal axis 114 of the rod first end 104 can be angled relative to the longitudinal axis 112 of the rod second end 106. The longitudinal axis 114 of the rod first end 104 can be parallel relative to the longitudinal axis 112 of the rod second end 106.

The extension 108, in various embodiments, can include a length 124 in the range of about two millimeters to about fifty millimeters (2 mm-50 mm), inclusive, among other lengths that are less than 2 mm or greater than 50 mm that is/are possible, each of which is contemplated herein. In some embodiments, the length 124 is in the range of about five millimeters to about thirty millimeters (5 mm-30 mm), inclusive, among other lengths that are less than 5 mm or greater than 30 mm that is/are possible, each of which is contemplated herein.

In various embodiments, the handle 100 can include a head 110 coupled to the rod 102. In some embodiments the head 110 is attached and/or coupled to the rod second end 106. The head 110, in at least some embodiments, can include an attachment mechanism 116a at a first end 120 of the head 110.

The attachment mechanism 116a can include any suitable attachment mechanism. Examples of an attachment mechanism 116a can include, but are not limited to, one or more threads, one or more complimentary locking contours, an aperture, a rod, a hook, one or more barbs, a screw, a locking screw, a nut, a bolt, a push screw, a clamp, and/or a spring button, etc., among other possible means of attachment, each of which is contemplated herein.

The head 110 can include a grip 122 on at least one exterior surface. The grip 122 can be a contour, a high friction surface, a high friction material, a knurling, and/or one or more grooves, etc., among other possible surfaces and/or materials that include(s) a high or relatively high coefficient of friction, each of which is contemplated herein.

The handle 100, in various embodiments, can include a coupler 130. In some embodiments, the coupler 130 can be removably coupled to the head 110. The coupler can be in a first position (see, e.g. FIG. 1), a second position (see, e.g., FIG. 2), or a position in between the first and second position. The coupler 130 can include an attachment mechanism 116*b* at a first end 132 configured to couple the coupler 130 to the head 110.

The attachment mechanism 116*b* can include any suitable attachment mechanism. Examples of an attachment mechanism 116*b* can include, but are not limited to, one or more threads, one or more complimentary locking contours, an aperture, a rod, a hook, one or more barbs, a screw, a locking screw, a nut, a bolt, a push screw, a clamp, and/or a spring button, etc., among other possible means of attachment, each of which is contemplated herein.

In various embodiments, the coupler 130 can include a grip 134 on at least one exterior surface. The grip 134 can be at least one contour, high friction surface, high friction material, among other possible surfaces and/or materials that include(s) a high or relatively high coefficient of friction, each of which is contemplated herein.

The coupler 130 can include a second attachment mechanism 136*a*, which can include one or more threads, one or more complimentary locking contours, an aperture, a rod, a hook, one or more barbs, a screw, a locking screw, a nut, a bolt, a push screw, a clamp, and/or a spring button, among other possible means of attachment, each of which is contemplated herein. The coupler 130, in various embodiments, can be cannulated 138 and/or hollow.

Referring now to FIGS. 9 through 18, the surgical system 10, at least in the illustrated embodiments, can include a gadget 200. As shown, the gadget 200 can include a body 202.

The body 202 can include at least one body attachment mechanism 204. The body attachment mechanism 204 can include one or more threads, one or more complimentary locking contours, an aperture, a rod, and/or a hook, etc. among other possible means of attaching the body 202 to the bone(s) of a subject, and/or other surgical device(s), each of which is contemplated herein.

In various embodiments, the gadget 200 can include a leg 206 coupled to the body 202 and attachable to the coupler 130. The leg 206 can include an attachment mechanism 136*b*, which can include one or more threads, one or more complimentary locking contours, an aperture, a rod, a hook, one or more barbs, a screw, a locking screw, a nut, a bolt, a push screw, a clamp, and/or a spring button, etc., among other possible means of attachment, each of which is contemplated herein. Attachment mechanism 136*b* can be complimentary to attachment mechanism 136*a*. In some embodiments, the leg 206 can include a slot 208 that can facilitate the coupling of the gadget 200 to the handle 100.

The gadget 200, in some embodiments, can include a slide 210 slidably coupled to the body 202. The slide 210 can be in a first closed position (see, e.g., FIGS. 14 and 16), a second fully extended position (see, e.g., FIGS. 15 and 17), or a third open position which can be any position in between the first closed position and the second fully extended position, (see, e.g., FIG. 10).

In various embodiments, the slide 210 can include a slide lock 212 coupled to the slide 210 and configured to hold the slide 210 in a desired position relative to the body 202. The lock 212, in various embodiments, can include a pressure fit, a post, an aperture, a screw, and/or a friction lock, etc., or other means of locking the slide in place relative to the body 202.

At least in the illustrated embodiment, the slide lock 212 can include an aperture 218 that can be threaded, and a post 220 that can be threaded and complimentary to the aperture 218. In some embodiments, the lock 212 can include a lock handle 222 that can be coupled to the lock post 220.

The lock handle 222 can be removable from (e.g., screwdriver) or integral with the lock post 220. In some embodiments, the lock post 220 forms at least a portion of a screw, or a bolt, among other locking mechanisms, each of which is contemplated herein. In various embodiments, the lock handle 222 can form at least a portion of a screwdriver, drill, etc., among other tools that create torque, each of which is contemplated herein.

In certain embodiments, the slide can include a radiograph positioning tool 214. The radiograph positioning tool 214 can include at least one of an aperture, a bar, text, and/or emoji, etc., among other possible tools, each of which is contemplated herein. At least in the pictured embodiment, the radiograph positioning tool 214 includes two bars 216 within the slide 210 at the same depth (e.g., on the same plane), but near opposing sides. When the slide 210 is viewed laterally with a radiograph, the two bars 216 can align (because both bars 216 are positioned at the same depth and/or on the same plane in the slide 210) (see, e.g., FIG. 12). The appearance of one bar 216 on the radiograph can indicate that the jig is properly aligned with the foot of a subject.

The gadget 200, in various embodiments, can include a guide body 230. The guide body 230 can be coupled to the slide 210 at an angle 250.

In certain embodiments, the guide body 230 can include an alignment tool 232 (see, e.g., FIG. 19) that indicates the guide body 230 is in the default position (see, e.g., FIG. 17) relative to the slide 210, where angle 250 (see, e.g., FIG. 19) is at a default angle (e.g., 0 degrees, or parallel).

Figure 18:
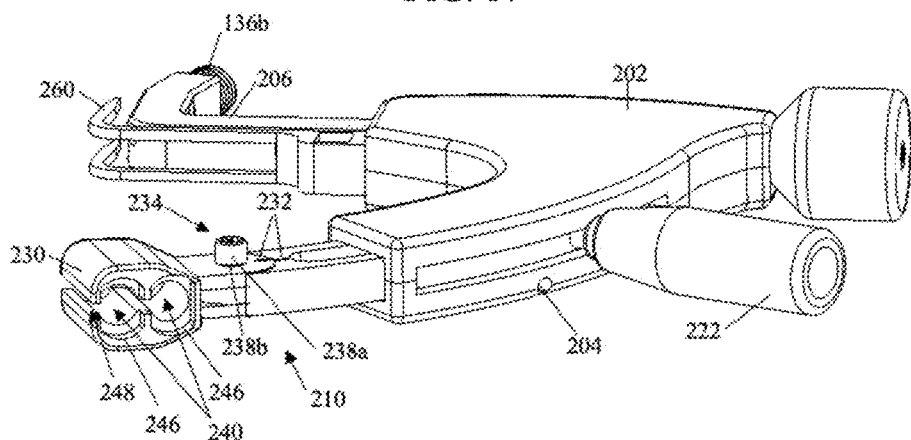
FIG. 18 is a schematic diagram illustrating an isometric view of the surgical system of FIG. 9 including a guide body.
Figure 19:
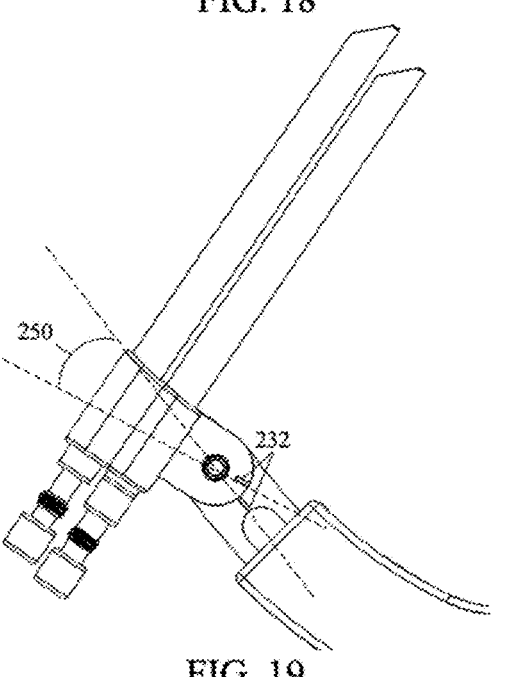
FIG. 19 is a schematic diagram illustrating a top view of the surgical system of FIG. 9 including a rotatable guide body.
Figures 20, 21, 22, 23:
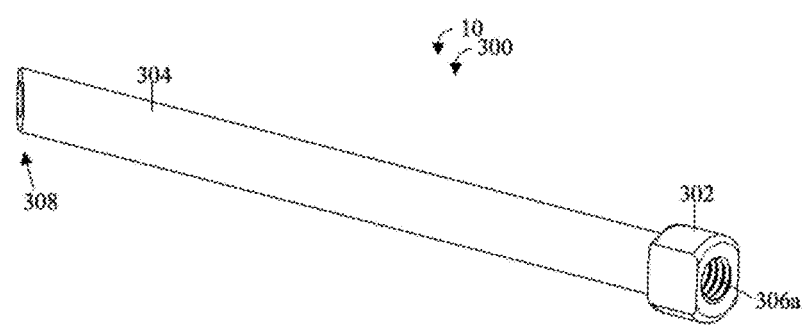
FIG. 20 is a schematic diagram illustrating an isometric view of an embodiment of the surgical system including a drill sleeve.
FIG. 21 is a schematic diagram illustrating a side view of the surgical system of FIG. 20.
FIG. 22 is a schematic diagram illustrating an end view of an embodiment of the surgical system of FIG. 20.
FIG. 23 is a schematic diagram illustrating an isometric view of an embodiment of the surgical system including a guide wire sheath.

In some embodiments, the guide body 230 can include a securing device 234 that locks the guide body 230 into place to prevent the angle 250 from changing when the securing device 234 is engaged (see, e.g., FIG. 18). The securing device 234, in various embodiments, can include least one of an aperture, a screw, a bolt, and/or a nut, etc., among other securing means, each of which is contemplated herein. In some embodiments the securing device 234 is a screw 238*a* and threaded aperture 238*b*.

In certain embodiments, the guide body 230 can include at least one sleeve aperture 240 configured to hold drill sleeve 300, as described in greater detail below. At least a portion of the sleeve aperture 240 can include any suitable shape, including, but not limited to, circular, oblong, square, rectangular, star, polygonal, and/or hexagonal, among other shapes that are possible, each of which is contemplated herein.

At least in the illustrated embodiment, the sleeve aperture 240 can include at least two shapes, a circular shape near the exit 244 and a non-circular shape at the entrance 246, among other suitable shapes and/or pairs of shape that are possible, each of which is contemplated herein. In some embodiments, the non-circular shape can assist in preventing the sleeve 300 from rotating.

The guide body 230 can also include slot 248 to assist in the removal of the gadget 200 from the foot of a subject without removing the k-wires. Removing the gadget 200 can give easier access to the k-wires for screw placement if not using the gadget 200 for screw placement.

Now referring to FIGS. 19 through 25, the gadget 200, in some embodiments, can include a drill sleeve 300. The drill sleeve 300 can include a head 302 and a shaft 304.

In some embodiments, the head 302 can include the same contours and/or geometry as the shaft 304. In other embodiments, the head 302 can have one or more different contours than the shaft 304. In at least the illustrated embodiment, the head 302 can include a non-circular contour, and the shaft 304 can include a circular contour.

The shaft 304, in various embodiments, can include complimentary contours to the sleeve aperture exit 244. In additional or alternative embodiments, the head 302 can include complimentary contours to the sleeve aperture entrance 246.

In some embodiments, the head 302 can include a coupling device 306a to removably couple the guide wire sheath 320 (see below) to the drill sleeve 300. The drill sleeve 300 can include a first end 308 that can be straight (e.g., a blunt cut) or not straight. In some embodiments the drill sleeve first end 308 can be chamfered. In other embodiments, the drill sleeve first end 308 can be configured to conform with human anatomy.

In various embodiments, the gadget 200 can include a guide wire sheath 320. The guide wire sheath 320 can include, among other features/components, a sheath head 322, a sheath shaft 324, and a coupling device 306b that is complimentary to the coupling device 306a. The coupling device(s) 306a and/or 306b can include one or more threads, one or more complimentary locking contours, an aperture, a magnet, a rod, a hook, one or more barbs, a screw, a locking screw, a nut, a bolt, a push screw, a clamp, and/or spring button, etc., among other possible means of coupling the guide wire sheath 320 to the drill sleeve 300, each of which is contemplated herein. The guide wire sheath 320, in some embodiments, is cannulated 326 to allow for a k-wire (e.g., a guide wire 276) to be inserted therethrough.

Figures 24, 25, 26, 27:
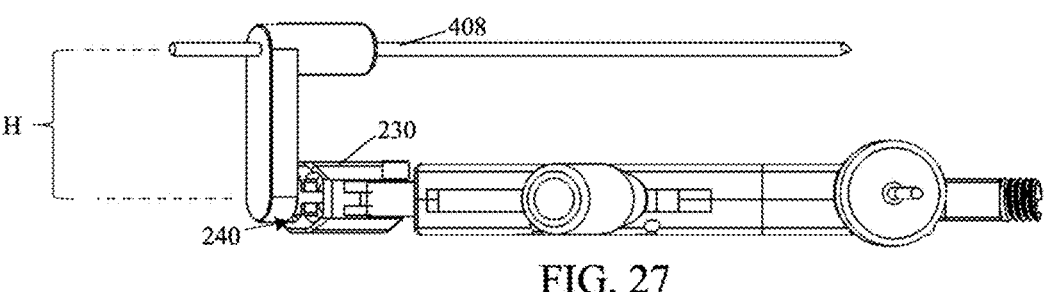
FIG. 24 is a schematic diagram illustrating a top view of an embodiment of the surgical system including two drill sleeves and guide wire sheaths.
FIG. 25 is a schematic diagram illustrating an isometric view of the surgical system of FIG. 19 including at least one drill sleeve and guide wire sheath.
FIG. 26 is a schematic diagram illustrating an isometric view of an embodiment of the surgical system including a periscope.
FIG. 27 is a schematic diagram illustrating an embodiment of the surgical system including a periscope.
Figure 28:
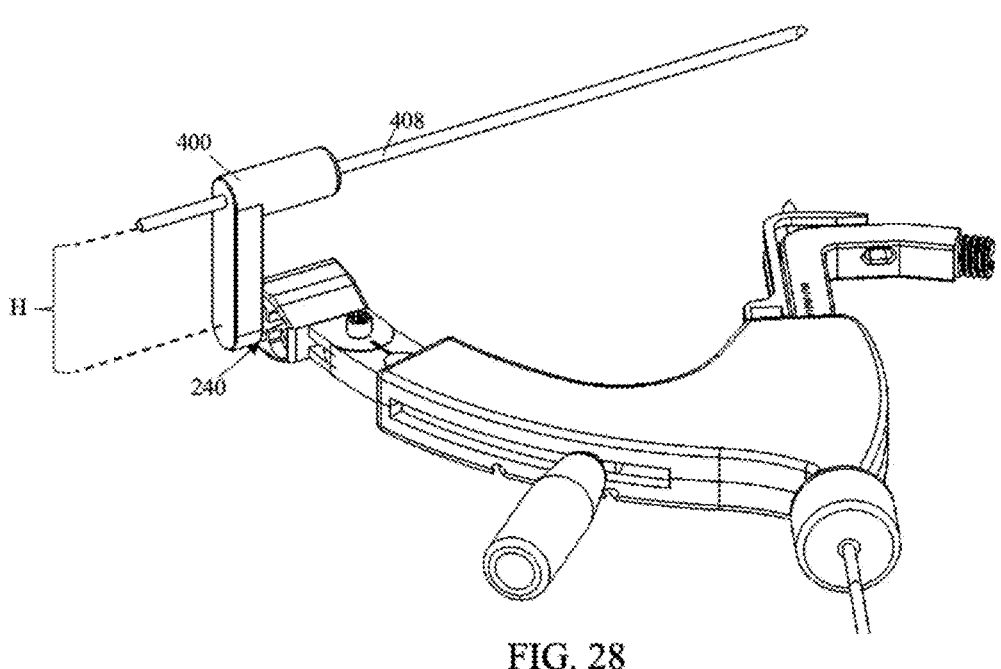
FIG. 28 is a schematic diagram illustrating an isometric view of the surgical system of FIG. 27.

Now referring to FIGS. 26 through 28, in various embodiments, the surgical system 10 can include at least one periscope 400. In some embodiments, the periscope 400 can include a post 402 that can be inserted into the sleeve aperture 240 to couple the periscope 400 to the guide body 230. In other embodiments, the periscope can be integral with the guide body 230.

The post 402, in various embodiments, can be configured to conform to the sleeve aperture 240. In certain embodiments, the periscope 400 can include at least one sight 404 including at least one sight aperture 406 in which the center of the sight aperture 406 is a height H from the center of the sleeve aperture 240.

The sight aperture 406, in various embodiments, can be configured to hold a k-wire or other instrument to be a sight wire 408. The height H can be any height that places the sight wire 408 above a patient's foot, typically in the range of about five millimeters to about one hundred millimeters (5 mm-100 mm), among other heights that are less than 5 mm or greater than 100 m, each of which is contemplated herein. In other embodiments, the height H can be any height in the range of about ten millimeters to about forty millimeters, among other possible heights, each of which in contemplated herein. In further embodiments, the height H can be about twenty-five millimeters (25 mm), among other possible heights, each of which in contemplated herein.

Figure 29:
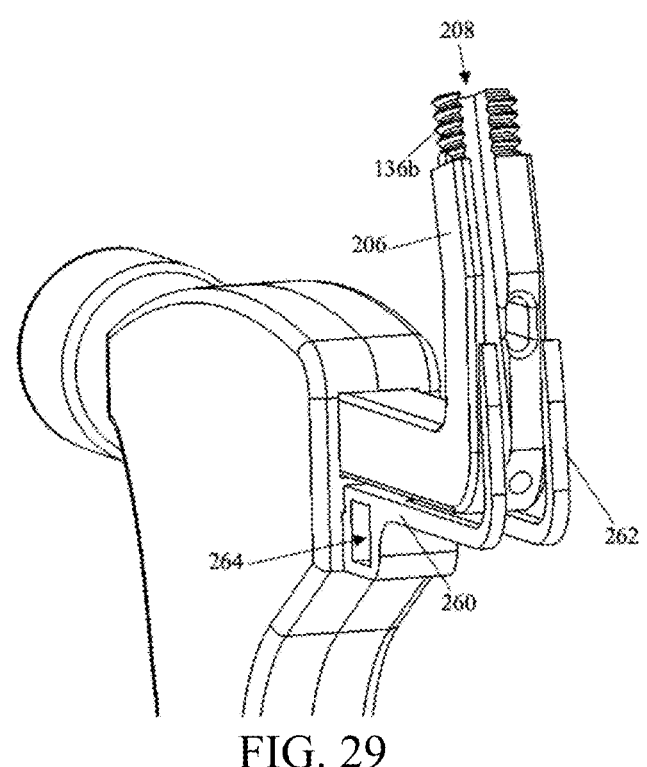
FIG. 29 is a schematic diagram illustrating an isometric view of an embodiment of the surgical system including a leg.
Figure 30:
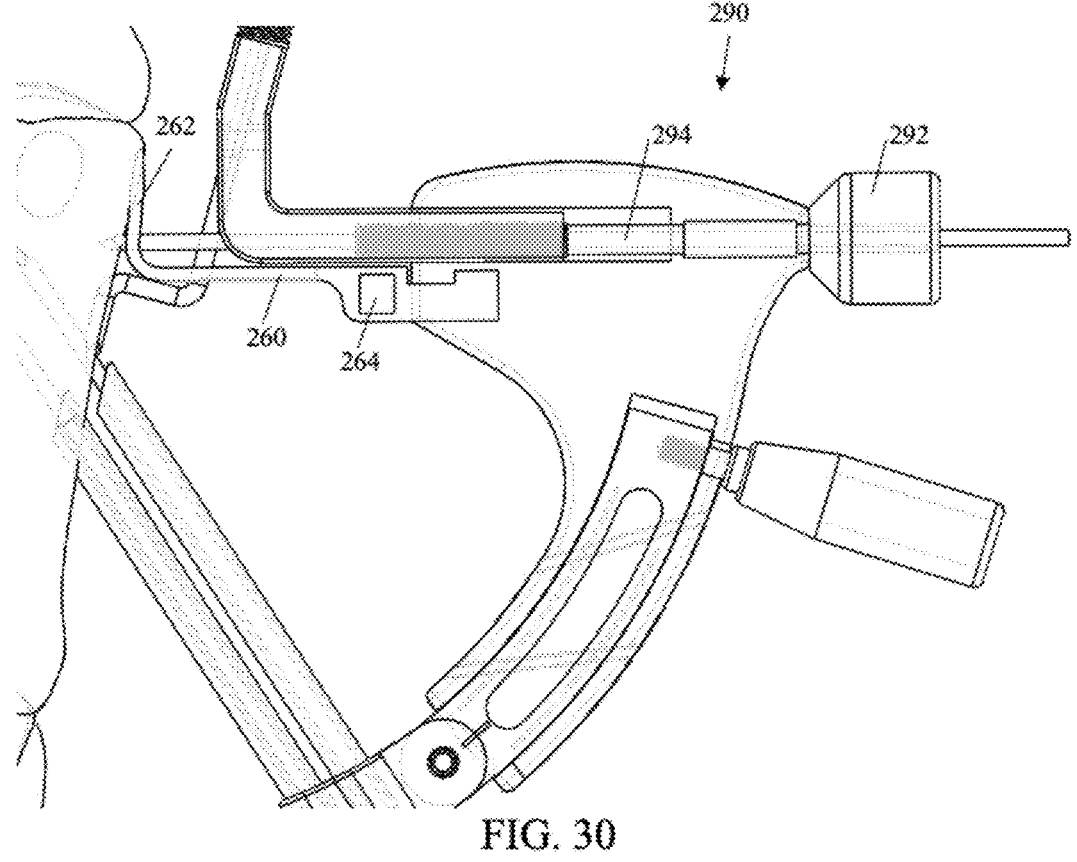
FIG. 30 is a schematic diagram illustrating a top view of an embodiment of the surgical system including a translator.

Now referring to FIGS. 29 through 30, in some embodiments, the gadget 200 can include a translator 290. The translator 290 can be any mechanism that can move a bone and/or bone portion in a plane (e.g., the transverse plane, etc.).

The translator 290, in various embodiments, can include an activation mechanism 292, such as, for example, a dial, a slide, a ratchet, or any other activation means, each of which is contemplated herein. At least in the illustrated embodiment, the translator 290 can include a dial 292 coupled to a rod 294 such that in response to the dial 292 being turned a first direction (e.g., clockwise), the rod 294 turns a first direction, and in response to the dial 292 being turned a second direction (e.g., counterclockwise), the rod 294 turns a second direction.

The rod 294, in various embodiments, is coupled to the leg 206 such that in response to the rod 294 being turned in the first direction, the leg 206 extends, and in response to the rod 294 being turned in the second direction, the leg 206 retracts. In some embodiments, the translator 290 can be cannulated.

The gadget 200, in various embodiments, can include a buttress 260 that can include at least one prong 262 or other device and/or contour that can dissipate a force over a surface. The buttress 260 can include an aperture 264. In some embodiments, the buttress 260 includes two prongs 262 spaced apart from one another. The prongs 262, in various embodiments, are configured to apply force to a bone and/or bone portion.

Figure 31:
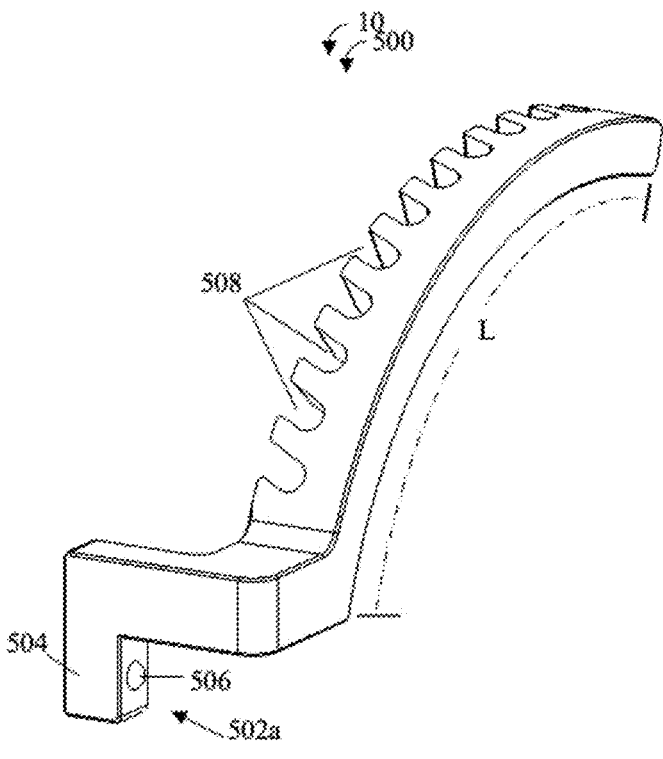
FIG. 31 is a schematic diagram illustrating an isometric view of an embodiment of the surgical system including a rotation arm.
Figure 32:
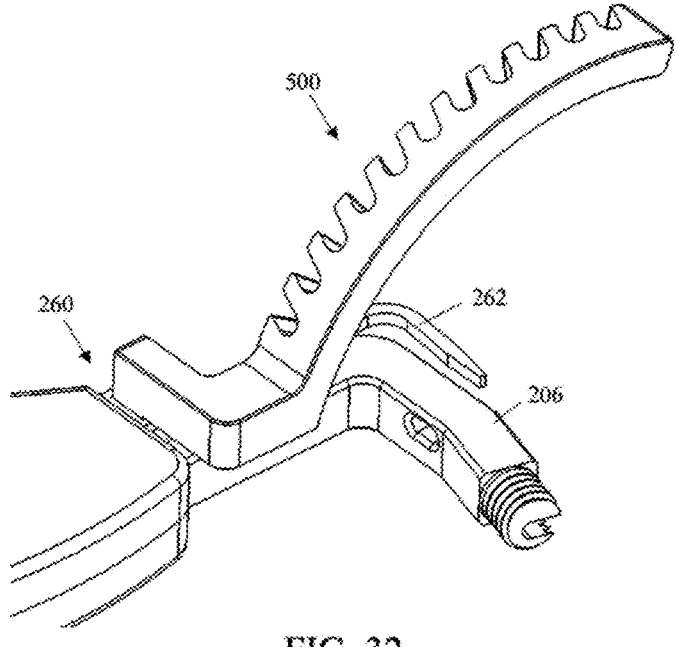
FIG. 32 is a schematic diagram illustrating an isometric view of an embodiment of the surgical system including a rotation arm.
Figure 33:
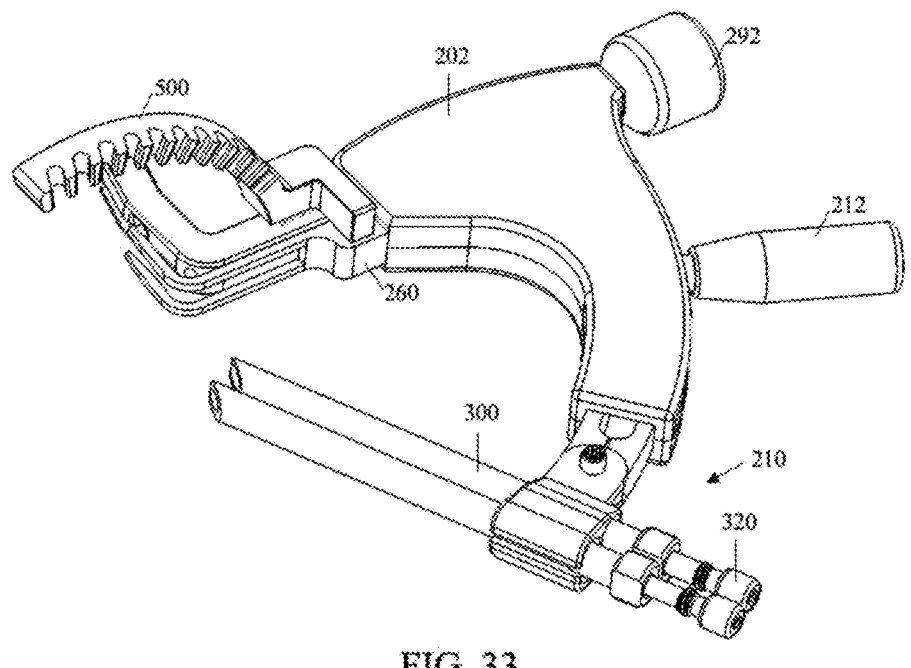
FIG. 33 is a schematic diagram illustrating an isometric view of an embodiment of the surgical system including a rotation arm.

Now referring to FIGS. 31 through 33, in some embodiments, the surgical system 10 can include a rotation arm 500. The rotation arm 500, in various embodiments, can be coupled to the gadget 200 through an attachment mechanism 502, which can include attachment mechanism(s) 502a, 502b.

The attachment mechanism 502a can include at least one of a set of threads, a post, an aperture, a shape, a detent, a ball, and/or a socket, or any other removably coupling means, each of which is contemplated herein. At least in the illustrated embodiment, the attachment mechanism 502a can include a post 504, and the attachment mechanism 502b can include an aperture 264. The attachment mechanism 502a can include a ball 506, and the attachment mechanism 502b can include a socket 266.

The rotation arm 500, in certain embodiments, can be coupled to any portion of the gadget 200 that remains stationary relative to the buttress. In at least one embodiment, the rotation arm 500 is coupled to the gadget 200 in response to placing the post 504 of a first shape into the aperture 264 of a complimentary shape. In some embodiments, the shape is non-circular, which can limit and/or eliminate rotation of the post 504 within the aperture 264.

The post 504 shape can include any suitable shape. In various embodiments, the shape of the post 504 includes at least one of square, hexagonal, octagonal, hourglass, cloverleaf, cross, star, oval, and/or wedge, etc., among other shapes that are possible, each of which is contemplated herein. In other embodiments, the post 504 includes a circular shape, and other means of controlling the rotation of the post 504 within the aperture 264 are employed.

The rotation arm 500, in various embodiments, can include at least one set of slots or notches 508. The notches 508 can be evenly spaced along a length L of the rotation arm 500, or they can be unevenly spaced along the length L of the rotation arm 500. In at least the illustrated embodiment, the notches 508 are evenly spaced to create approximately five degrees (5°) of rotation for each notch 508, among other rotational angles that are less than 5° or greater than 5°, each of which is contemplated herein.

In some embodiments, the notches can be spaced further apart to create degree changes of greater than 5°. In other embodiments, the notches can be spaced closer together to create degree changes of less than 5°.

Figure 34:
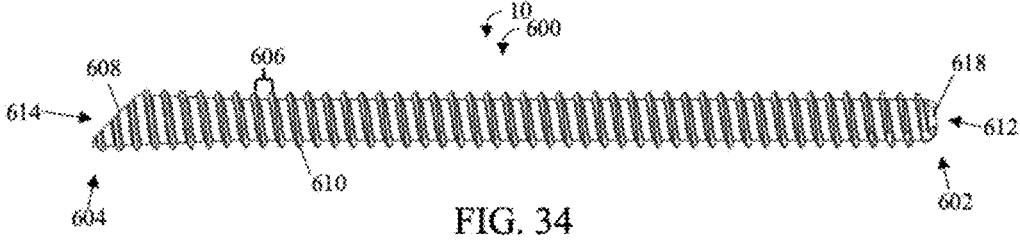
FIG. 34 is a schematic diagram illustrating a side view of an embodiment of the surgical system including a screw.
Figure 35:
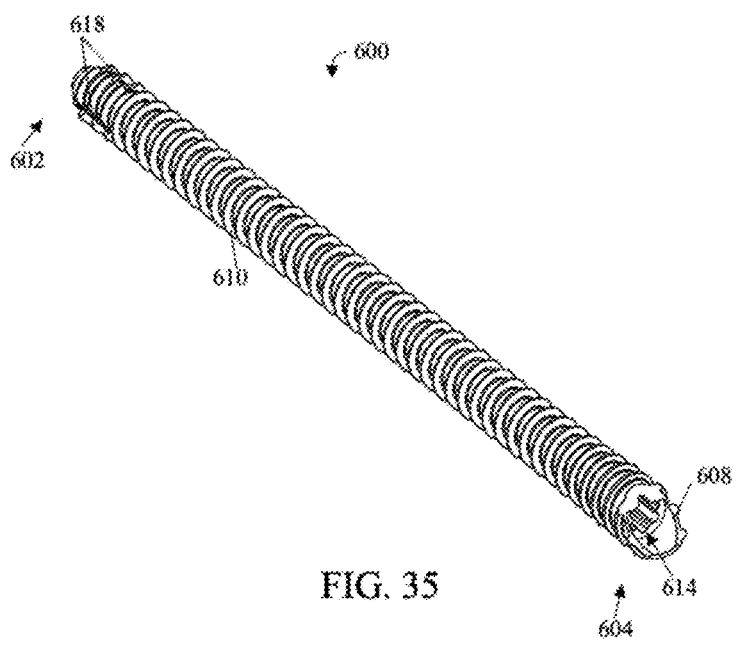
FIG. 35 is a schematic diagram illustrating an isometric view of the surgical system of FIG. 34.
Figure 36:
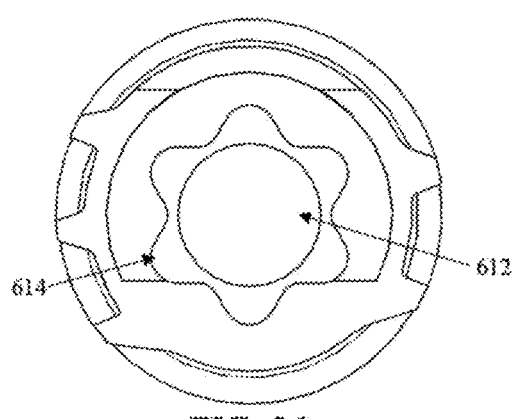
FIG. 36 is a schematic diagram illustrating an end view of the surgical system of FIG. 34.
Figures 37, 38:
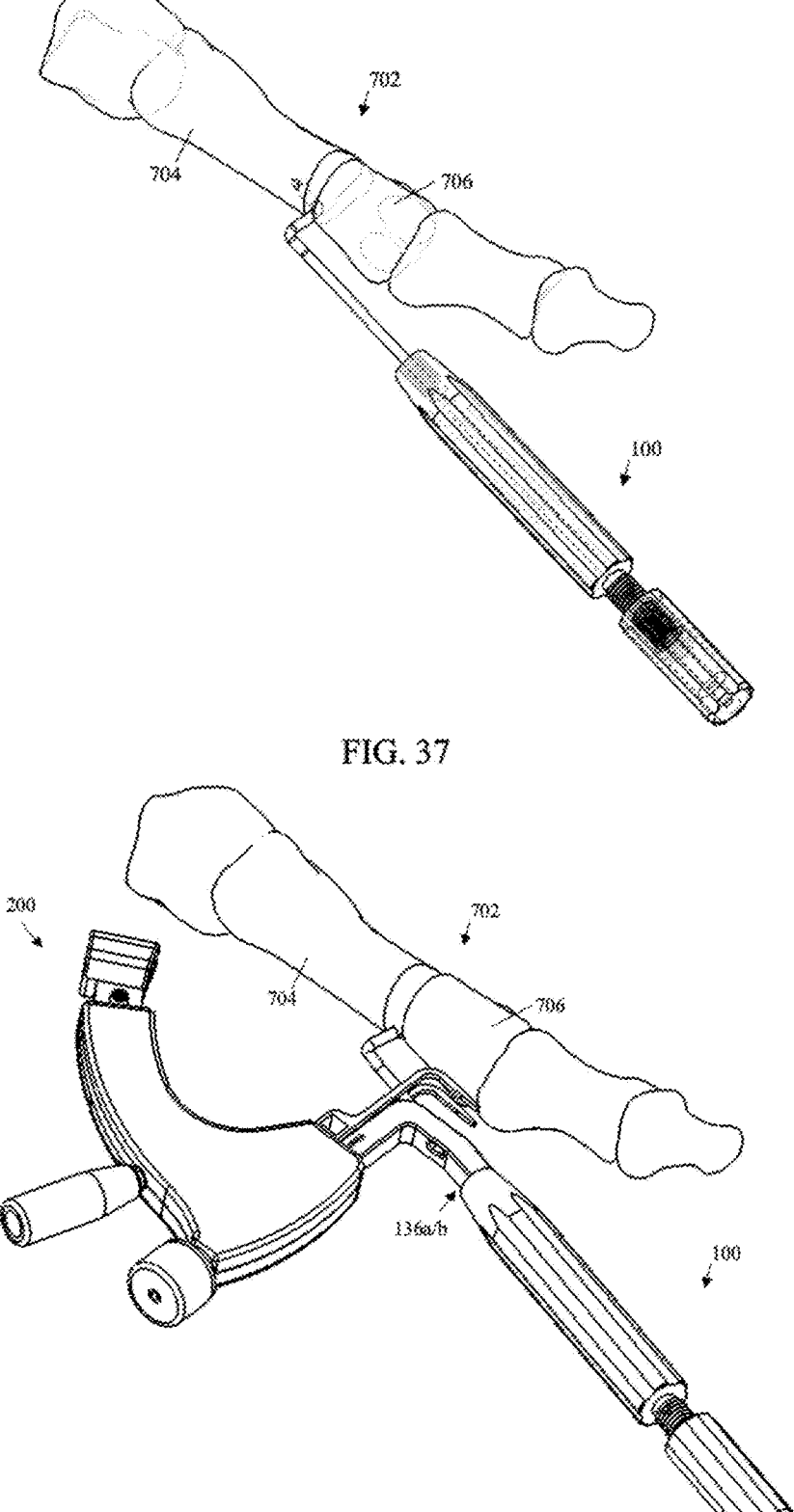
FIG. 37 is of a schematic diagram illustrating the surgical system of FIG. 1 with the handle inserted into the bone of a subject.
FIG. 38 is a schematic diagram illustrating the surgical system of FIG. 1 coupled to the gadget of FIG. 9.
Figure 39:
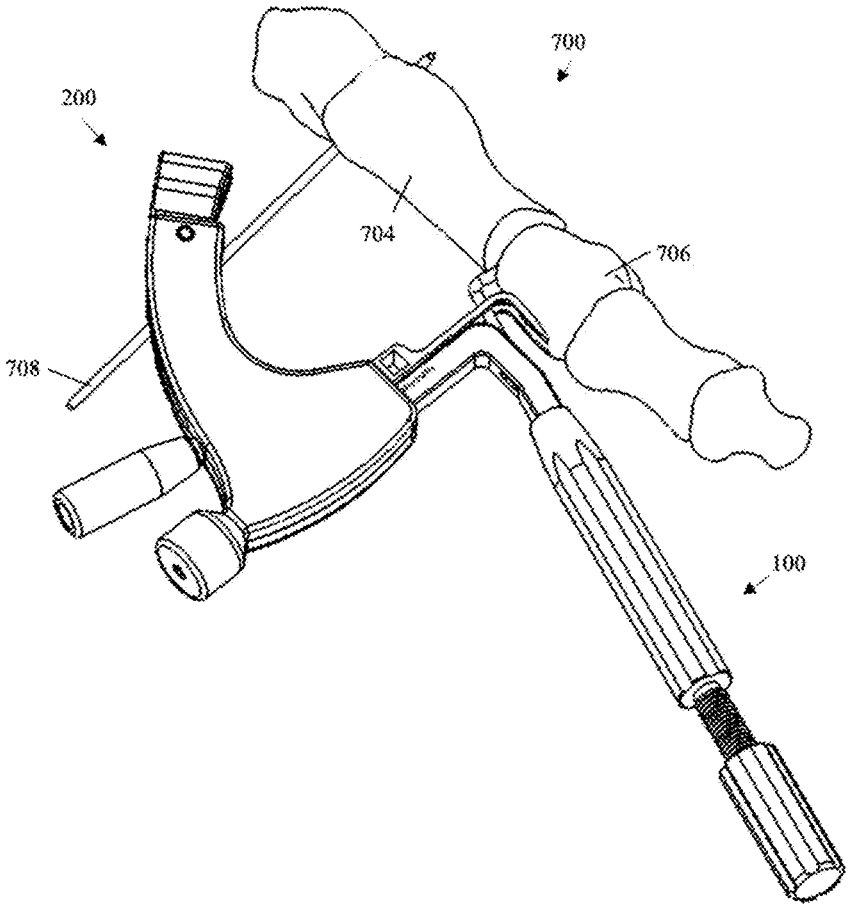
FIG. 39 is a schematic diagram illustrating the surgical system of FIG. 1 coupled to the gadget of FIG. 9 including an attachment mechanism.
Figure 40:
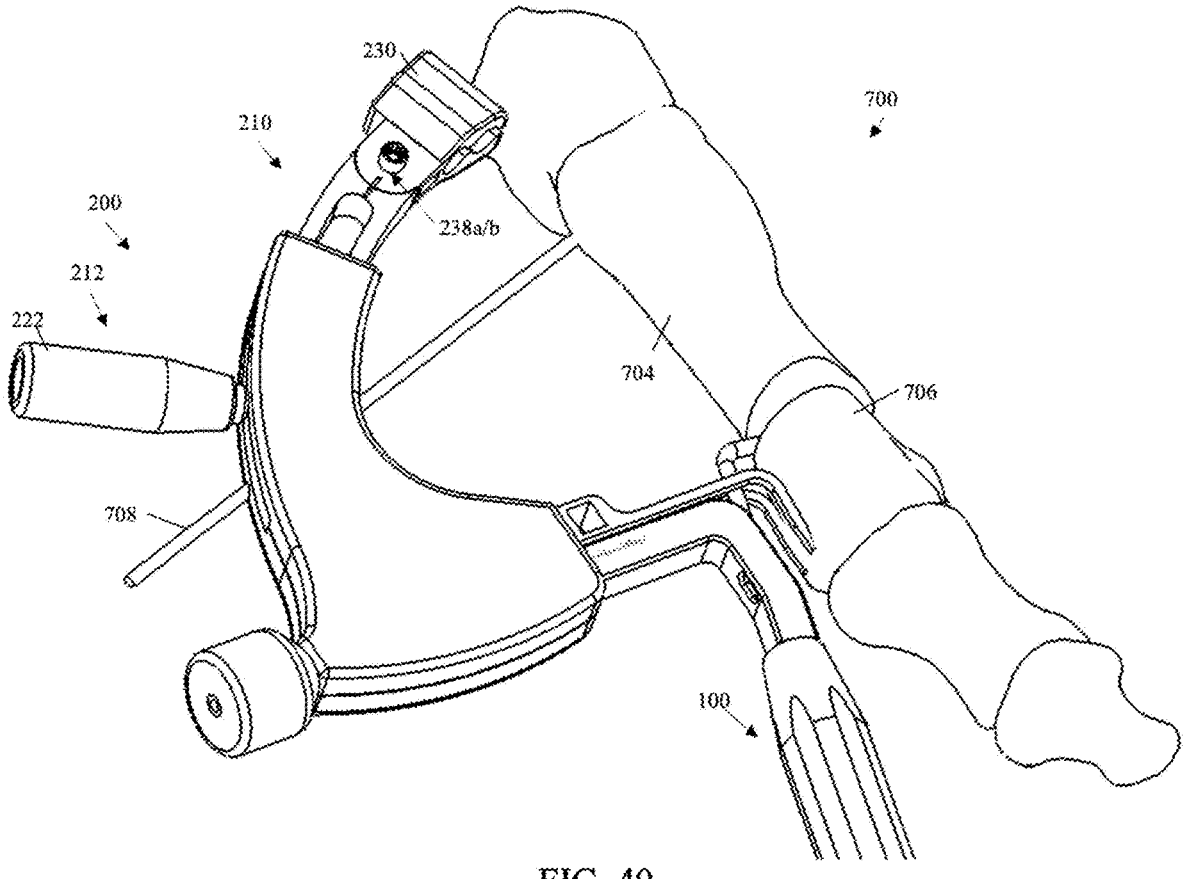
FIG. 40 is a schematic diagram illustrating the surgical system of FIG. 1 coupled to the gadget of FIG. 9 including an open slide.
Figure 41:
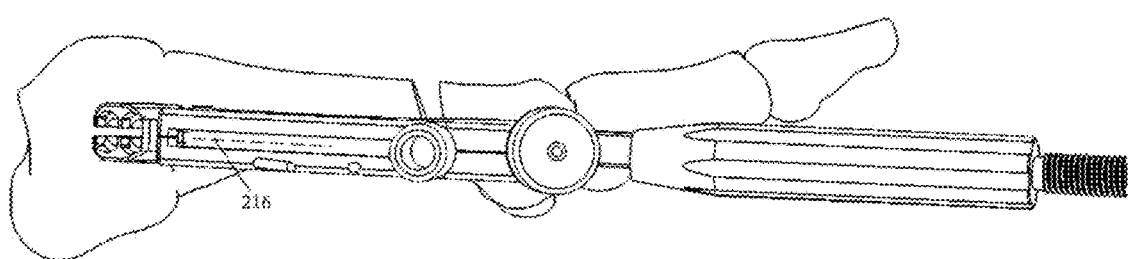
FIG. 41 is a schematic diagram illustrating the surgical system of FIG. 1 coupled to the gadget of FIG. 9 including a radiograph positioning tool.
Figure 42:
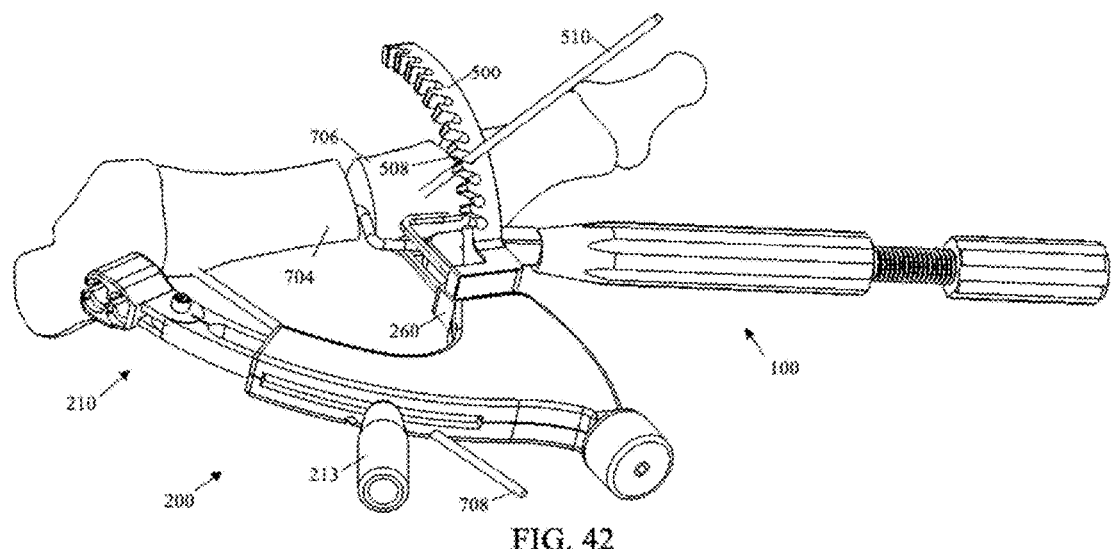
FIG. 42 is a schematic diagram illustrating the surgical system of FIG. 1 coupled to the gadget of FIG. 9 including a rotation arm.
Figure 43:
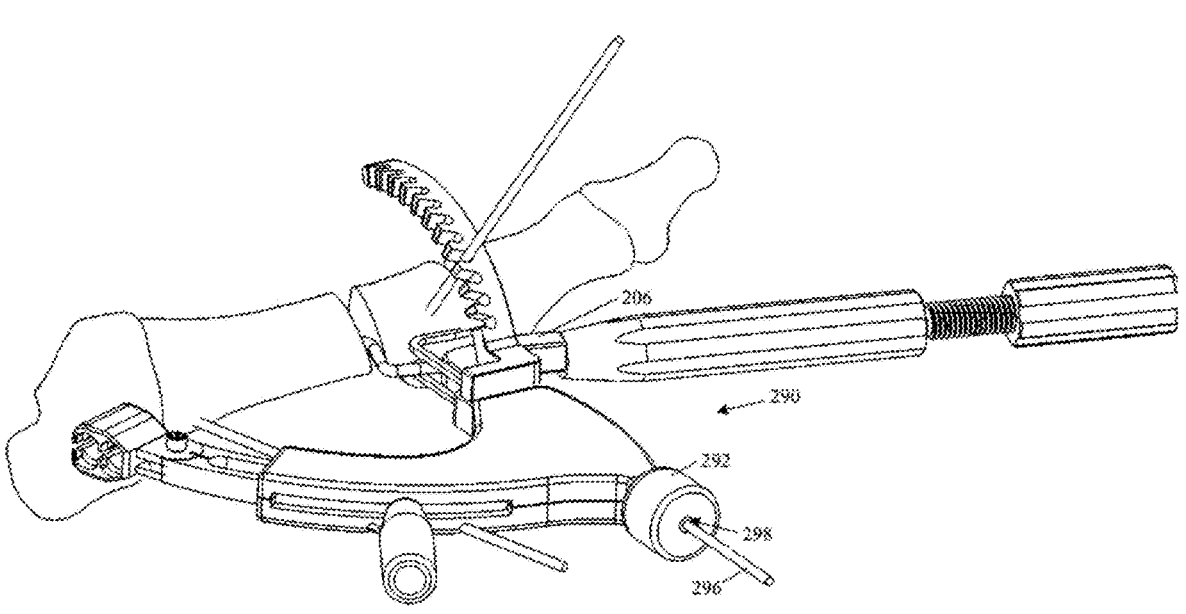
FIG. 43 is an isometric view of a schematic diagram illustrating the surgical system of FIG. 42 including a k-wire.

Now referring to FIGS. 34 through 36, in some embodiments, the surgical system 10 can include at least one screw 600. The screw 600, in various embodiments, can be fully threaded, or partially threaded.

In some embodiments, the screw 600 can be threaded at the first end 602. In additional or alternative embodiments, the screw 600 can be threaded at the second end 604. In certain embodiments, the screw 600 can include at least a portion of the shaft between the first end 602 and the second end 604, which can be non-threaded (e.g., smooth). In at least one embodiment, all the threads on screw 600 can include the same pitch 606 so as to not create compression or distraction as the screw 600 is inserted into bone portions (e.g., bones 704 and 706).

In one or more embodiments, the second end 604 can include a chamfered shape 608. The chamfer shape 608 can be configured to conform to the shape of a bone (e.g., a proximal metatarsal 704).

In various embodiments, the screw 600 can include a longitudinal aperture 612 (e.g., the screw 600 can be canulated). Additionally, or alternatively, the aperture 612 can be circular so as to conform to the shape of a k-wire.

The aperture 612, in some embodiments, can be non-circular so as to conform to a different k-wire shape, or for other reasons. For example, the aperture 612 can be hexagonal, square, oval, or other shape(s), each of which is contemplated herein.

In some embodiments, the screw can have an aperture 614 that is configured to conform to a screwdriver, or other driving tool and/or similar tool. In various embodiments, the first end 602 can include a self-tapping and/or self-drilling geometry 618, which can eliminate the need for pre-drilling.

The following example procedure shown in FIG. 52 is of a bunion correction procedure, however, the surgical system 10 can be useful in other surgical procedures and/or other bones and/or bone portions. It is to be noted that the example procedure is intended as a guide to understanding the various embodiments disclosed herein and not to limit the various embodiments in any manner.

In FIG. 52, an osteotomy (or other procedure) can be performed on a metatarsal 702 to separate the capital fragment 706 from the proximal metatarsal 704 (block 802). The rod first end 104 is placed within the proximal metatarsal 704, preferably within the medullary canal (block 804) (see, e.g., FIG. 37).

The gadget 200 is coupled to the handle 100 by engaging the second attachment mechanism 136a/b. In at least one embodiment, the attachment mechanism 136a/b can be complimentary threads and the gadget 200 is coupled to the handle 100 by screwing the coupler 132 to the leg 206 (block 806) (see e.g., FIG. 38).

The gadget 200 can be secured to a foot 700 of a subject by engaging the body attachment mechanism 204. In at least one embodiment, engaging the body attachment mechanism 204 includes inserting a k-wire 708 through the body aperture 205 (block 808) (see, e.g., FIG. 39).

The slide 210 can be extended until it contacts the side of the foot 700 (see, e.g., FIG. 40) (block 810). The slide lock 212 is then engaged.

In some embodiments, the slide lock 212 is engaged by rotating the lock handle 222 in a first direction (e.g., clockwise). The position of the guide body 230 can be evaluated.

If adjustment of the guide body 230 position is desired, the securing device 234 can be disengaged to allow for adjustment (block 812). In at least the illustrated embodiment, the securing device 234 includes the screw 238a and the aperture 238b. The securing device 234 can be disengaged by loosening the screw 238a, the position of the guide body 230 can be adjusted (i.e. the angle 250 is increased or decreased), and the securing device 234 can be re-engaged by tightening the screw 238a.

The alignment of the gadget 200 with the foot 700 can be confirmed radiographically (block 814). In some embodiments, the radiograph positioning tool 214 includes two bars 216 placed at opposing sides of the slide 210, but at the same depth. When viewed transversely, the two bars 216 will appear to be one bar (because they are aligned, or in the same plane) and appear to align with the longitudinal axis of the metatarsal 702 (see, e.g., FIG. 41) (block 816).

The capital fragment 706 can be rotated. This can be accomplished freehand, or a k-wire 510 can be inserted into the capital fragment 706. The k-wire 510 can act as a lever for manual rotation, and/or the rotation arm 500 can be utilized.

The rotation arm 500 can be coupled to the gadget 200 and/or any other portion of the surgical system 10 that remains stationary with respect to the capital fragment 706. In some embodiments, the rotation arm 500 can be coupled to the buttress 260 by placing the square post 504 into the complimentary aperture 264 which places the ball 506 in the socket 266. The k-wire 510 can be used as a lever to rotate the capital fragment 706, and then placed within a notch 508 to hold the rotation (see, e.g., FIG. 42).

A k-wire 296 can be placed through aperture 298 and into the capital fragment 706 (see, e.g., FIG. 43) to maintain the rotated position of the capital fragment 706. Optionally, the rotation arm 500 and the k-wire 510 can be removed.

The capital fragment can be translated to the desired position (block 818). The capital fragment 706 can be moved transversely freehand, or by utilizing the translator 290.

Figure 44:
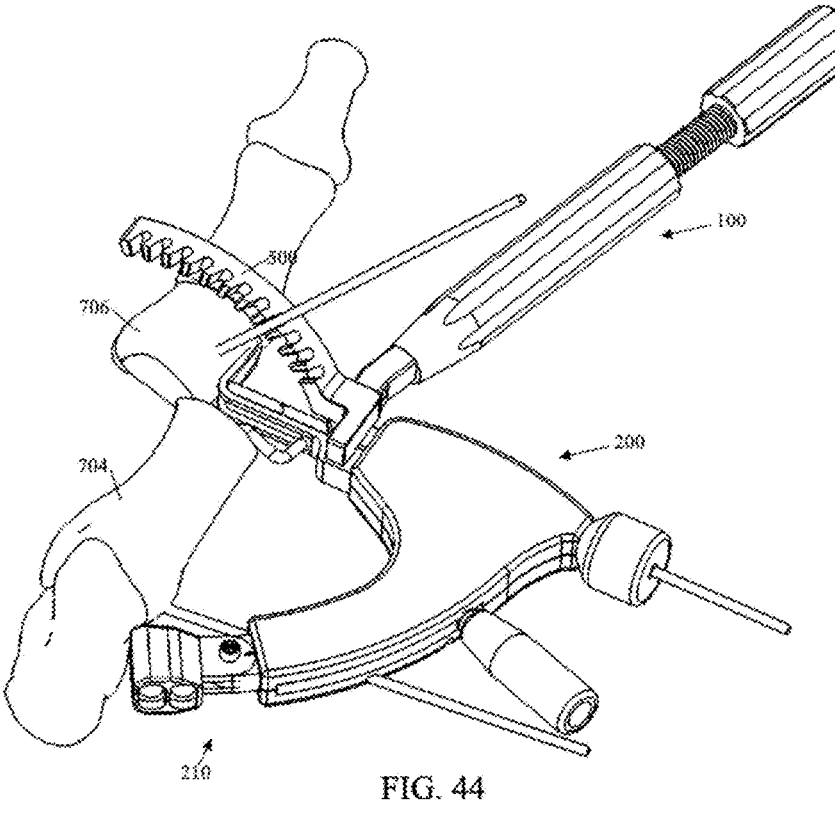
FIG. 44 is an isometric view of a schematic diagram illustrating the surgical system of FIG. 43 including a translated capital fragment.
Figure 45:
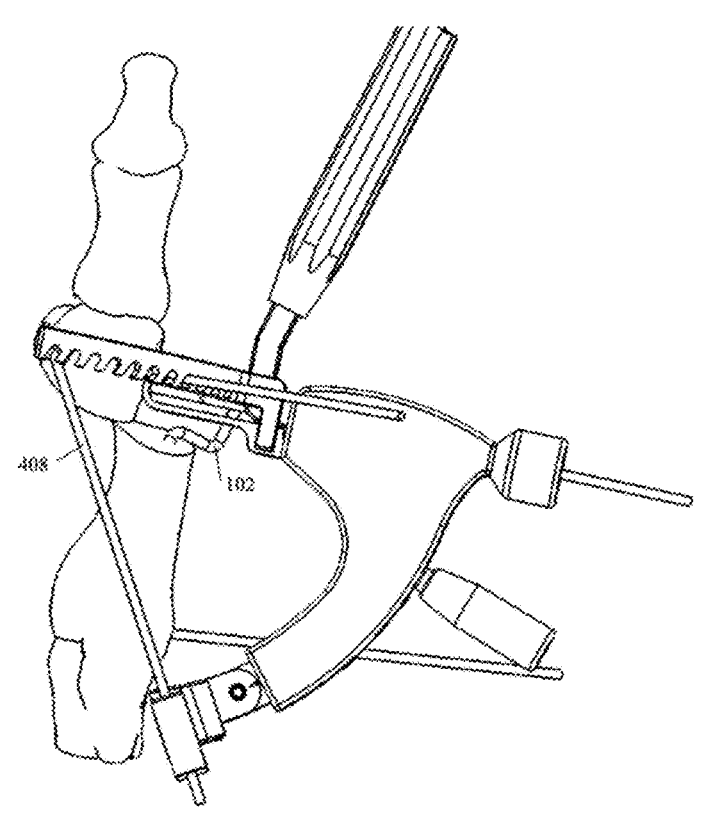
FIG. 45 is a schematic diagram illustrating a top view the surgical system of FIG. 44.
Figure 46:
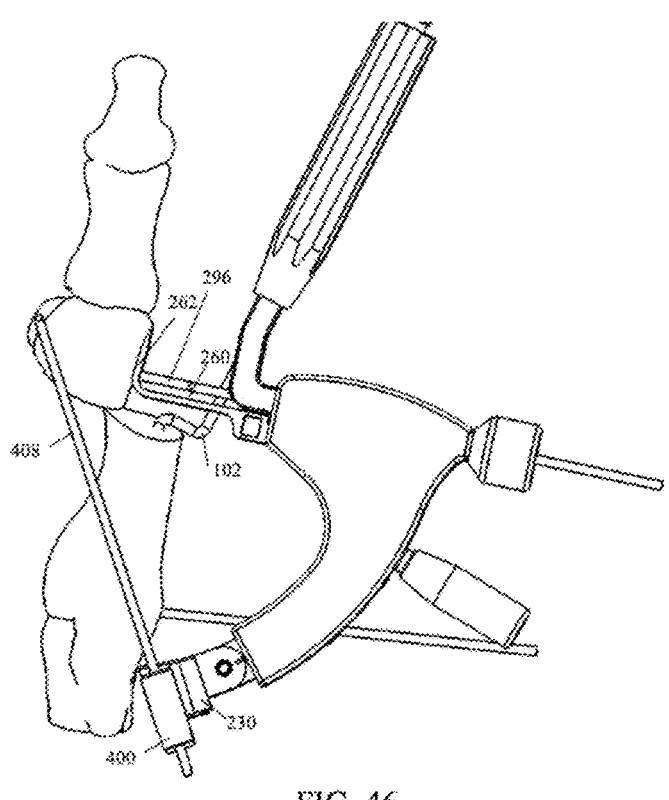
FIG. 46 is a schematic diagram illustrating the surgical system of FIG. 45 including a periscope.
Figure 47:
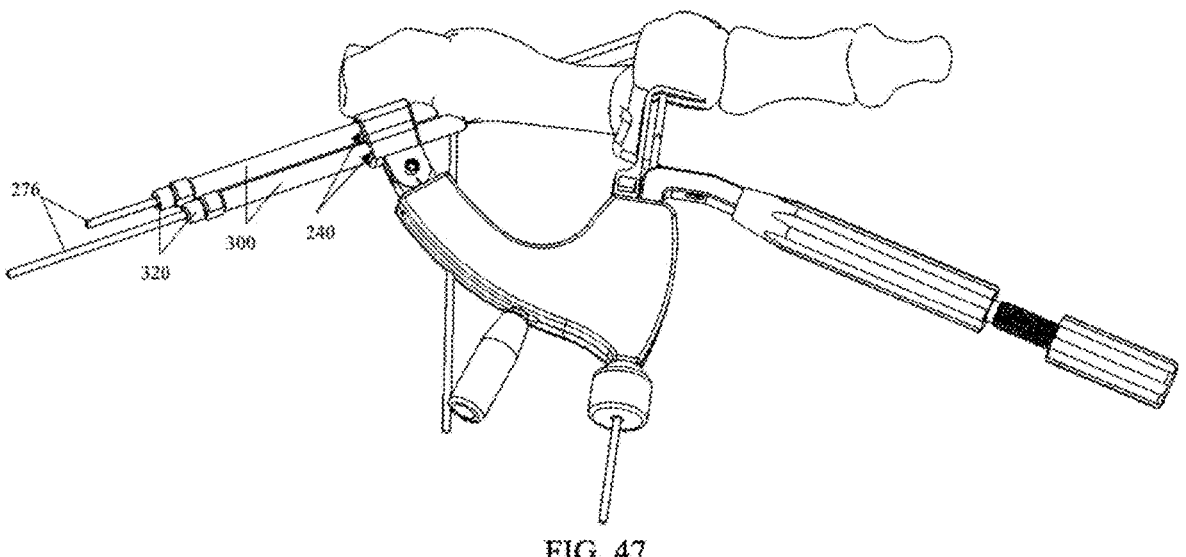
FIG. 47 is a schematic diagram illustrating of the surgical system of FIG. 46 including a drill sleeve and a guide wire sheath.
Figure 48:
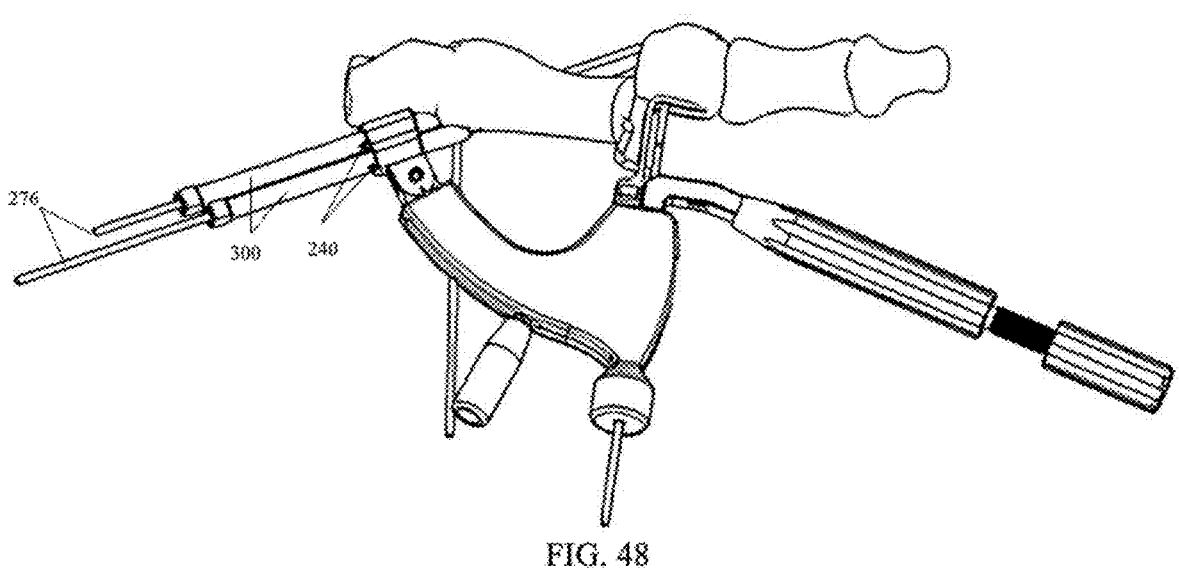
FIG. 48 is a schematic diagram illustrating the surgical system of FIG. 47 without a guide wire sheath.
Figure 49:
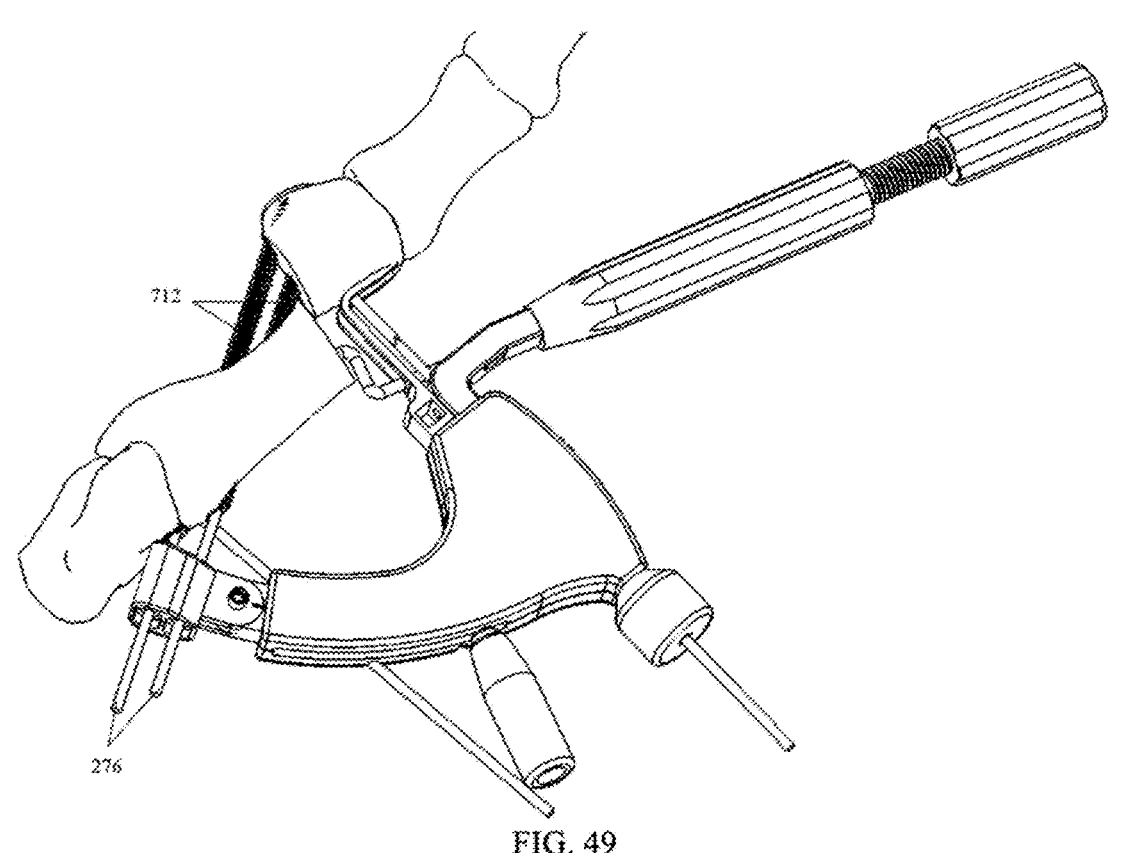
FIG. 49 is a schematic diagram illustrating the surgical system of FIG. 48 with screws.
Figure 50:
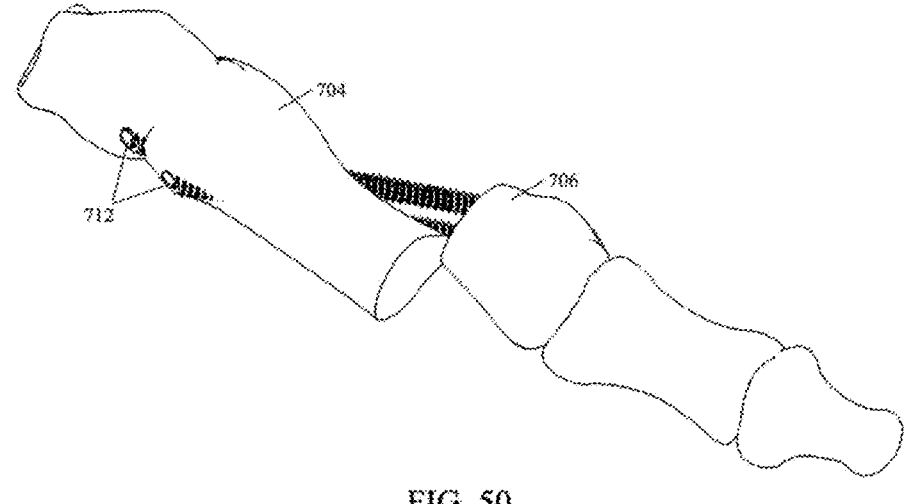
FIG. 50 is a schematic diagrams illustrating a dorsal view the surgical system of FIG. 48 with the gadget and handle removed.
Figure 51:
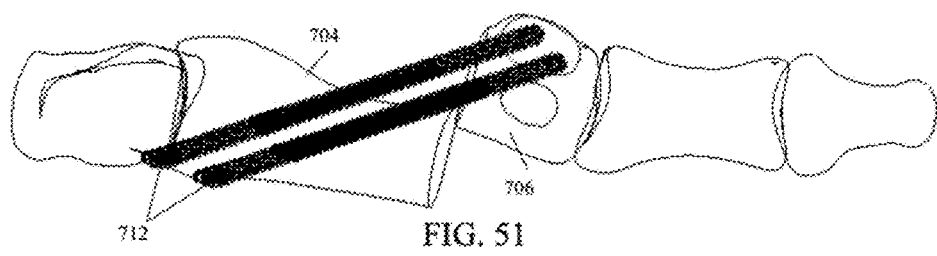
FIG. 51 is a schematic diagrams illustrating a plantar view the surgical system of FIG. 50.

To utilize the translator 290, the dial 292 can be rotated to retract the leg 206, placing force(s) between the proximal metatarsal 704 (through the rod first end 104) and the capital fragment (through the buttress 260), thus moving the capital fragment 706 in the transverse direction to a target and/or desired location (e.g., see FIGS. 44 and 45).

In some embodiments, the buttress 260 is configured to abut the skin of a subject. In other embodiments, the buttress 260 is configured to abut the capital fragment 706 of a subject (e.g., being placed between the skin and the capital fragment).

In some embodiments, a periscope 400 can be employed to visualize screw placement (block 820). A periscope post 402 can be placed in the sleeve aperture 240 and a sight wire 408 can be placed in the sight aperture 406.

The sight wire 408 can extend over the foot 700. An AP radiograph can be taken, the future position/planned placement of screw 712 can be indicated by the k-wire 408 on the radiograph. The future position of screw 712 can be altered by adjusting the guide body 230 (see, block 812) and the slide 210 (see, block 810) (see, e.g., FIG. 45). If the rotation arm 500 is in the way of viewing the future position of the screw 600, it can be removed (see, e.g., FIG. 46). In some embodiments, the periscope can include a radiograph positioning tool 214 to assist in proper visualization. In one or more embodiments the radiograph positioning tool 214 can include an aperture.

The drill sleeve 300 and the guide wire sheath 320 can be placed in the sleeve aperture 240, and guide wire(s) 276 (k-wires) can be placed through the sheath(s) 320 into the proximal metatarsal 704 and into the capital fragment 706 (see, e.g., FIG. 47) (block 822). The position of the k-wires can be checked radioscopically (block 824).

Optionally, the guide wire sheath 320 can be removed from the drill sleeve 300. In some embodiments, the sheath 320 can be removed by unscrewing the sheath 320 from the sleeve 300 (block 826). The bone(s) can be prepped by pre-drilling (e.g., using the drill sleeve 300 to guide the drill (see, e.g., FIG. 48)).

The drill sleeve 300 can be removed from the sleeve aperture 240 (block 828). The screw 600 can be placed over the guide wire 276. The screw 600 is placed through the proximal metatarsal 704 and into the capital fragment 706 (see, e.g., FIG. 49).

The screw 600 can be placed so that the chamfer 608 approximately aligns with the proximal metatarsal 704 edge. Aside from the screw(s) 600, the rest of the surgical system 10 can be removed (see, e.g., FIGS. 50 and 51).

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

The invention claimed is:

1. A surgical apparatus comprising:
a handle configured to be couplable to a gadget, the handle comprising:
    a rod including a first end and a second end opposite the first end;
    the first end comprising a first longitudinal axis and the second end comprising a second longitudinal axis, wherein the first longitudinal axis is offset from the second longitudinal axis by an extension; and
    a coupler coupled to the rod the coupler comprising a threaded first end;
    wherein the gadget comprises;
    a leg comprising:
        a slot including an open side, a slot longitudinal axis, and a slot threaded first end, wherein the slot threaded first end is configured to conform to the coupler threaded first end to facilitate the coupling of the handle to the leg;
        a slide slidably coupled to a body; and
        a guide body coupled to the slide and configured to position a guide wire,
        wherein the guide body is configured to be rotatable.

2. The surgical apparatus of claim 1, further comprising:
a translator comprising the passage and a post, wherein the passage and the post include complimentary threads such that rotating the post within the passage in a first rotational direction controls the extension of the leg, and rotating the post within the passage in a second rotational direction controls the retraction of the leg.

3. The surgical apparatus of claim 2, wherein the slide includes a slide lock configured to prevent the slide from moving when the slide lock is engaged.

4. The apparatus of claim 2, further comprising a rotation arm removably couplable to the body and configured to facilitate the rotation of a first bone portion, wherein the rotation arm comprises at least one notch configured to hold a k-wire.

5. The surgical apparatus of claim 4, wherein the rotation arm is configured to facilitate the rotation of a metatarsal capital fragment.

6. The surgical apparatus of claim 2, further comprising a periscope configured to couple to the body and hold a k-wire in the same orientation that a guide wire sheath will guide a screw.

7. The surgical apparatus of claim 6, wherein the periscope further comprises a radiograph alignment tool.

8. The surgical apparatus of claim 1, further comprising a radiograph positioning tool including two metal rods positioned within the slide such that they appear as one rod when viewed laterally.

9. The surgical apparatus of claim 1, further comprising a guide wire sheath coupled to the body, wherein the guide wire sheath is configured to guide a k-wire to a desired position.

10. The surgical apparatus of claim 1, wherein the handle further comprises:
a coupler first end and a coupler second end opposite the coupler first end; and
a head coupled to the rod second end and couplable to the coupler second end.

11. The surgical apparatus of claim 1, wherein the first longitudinal axis and the second longitudinal axis are parallel.

12. The apparatus of claim 1, wherein the extension comprises an extension length in the range of 2 mm-50 mm inclusive.

13. A method comprising the steps of:
providing an apparatus, wherein the apparatus comprises:
    a rod including a first end and a second end opposite the first end;
    the first end including a first longitudinal axis and the second end including a second longitudinal axis, wherein the first longitudinal axis and the second longitudinal axis are not coextensive;
    a coupler coupled to the rod;
    a leg comprising:
        a slot including an open side, a slot longitudinal axis, and a slot threaded first end, wherein the slot threaded first end is configured to conform to the coupler threaded first end to facilitate the coupling of the handle to the leg;
        a slide slidably coupled to a body; and
        a guide body coupled to the slide and configured to position a guide wire, wherein the guide body is configured to be rotatable; and
    inserting the rod first end into a proximal metatarsal bone portion.

14. The method of claim 13, further comprising:
placing the slot onto the rod and coupling to coupler to the leg.

15. The method of claim 14, further comprising providing a buttress coupled to the body and abutting a first bone.

16. The method of claim 15, further comprising checking the position of the gadget relative to the first bone by viewing the radiograph positioning tool from a lateral view, wherein the radiograph positioning tool comprises at least two bars within the body that will appear as one bar when viewed from a lateral position on a radiograph when the gadget is in a desired position relative to the first bone.

17. The method of claim 16, further comprising providing a translator, wherein the translator extends and retracts the leg and handle relative to the buttress wherein the extension or retraction of the leg is controlled by the translator.

\* \* \* \* \*